US010195215B2

(12) United States Patent
Genberg et al.

(10) Patent No.: US 10,195,215 B2
(45) Date of Patent: *Feb. 5, 2019

(54) METHODS FOR REDUCING CELLULAR PROLIFERATION AND TREATING CERTAIN DISEASES

(71) Applicants: Carl Genberg, Las Vegas, NV (US); Paul B. Savage, Mapleton, UT (US)

(72) Inventors: Carl Genberg, Las Vegas, NV (US); Paul B. Savage, Mapleton, UT (US)

(73) Assignee: BRIGHAM YOUNG UNIVERSITY, Provo, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 15/895,848

(22) Filed: Feb. 13, 2018

(65) Prior Publication Data
US 2018/0169114 A1 Jun. 21, 2018

Related U.S. Application Data

(63) Continuation of application No. 14/149,675, filed on Jan. 7, 2014, now Pat. No. 9,943,529.

(60) Provisional application No. 61/749,800, filed on Jan. 7, 2013.

(51) Int. Cl.
A61K 31/575 (2006.01)
A61K 31/56 (2006.01)

(52) U.S. Cl.
CPC ............ A61K 31/575 (2013.01); A61K 31/56 (2013.01)

(58) Field of Classification Search
CPC .................. A61K 31/575; A61K 31/56
See application file for complete search history.

(56) References Cited

U.S. PATENT DOCUMENTS

| | | |
|---|---|---|
| 4,248,236 A | 2/1981 | Linder |
| 4,296,206 A | 10/1981 | Simons |
| 4,661,341 A | 4/1987 | Benedict et al. |
| 4,723,950 A | 2/1988 | Lee |
| 4,842,593 A | 6/1989 | Jordan et al. |
| 4,865,855 A | 9/1989 | Hansen et al. |
| 4,972,848 A | 11/1990 | Di Domenico |
| 5,025,754 A | 6/1991 | Plyler |
| 5,286,479 A | 2/1994 | Garlich et al. |
| 5,310,545 A | 5/1994 | Eisen |
| 5,356,630 A | 10/1994 | Laurencin et al. |
| 5,364,650 A | 11/1994 | Guthery |
| 5,380,839 A | 1/1995 | McCall et al. |
| 5,552,057 A | 9/1996 | Hughes et al. |
| 5,624,704 A | 4/1997 | Darouiche et al. |
| 5,687,714 A | 11/1997 | Kolobow |
| 5,721,359 A | 2/1998 | Dunn et al. |
| 5,763,430 A | 6/1998 | Zasloff |
| 6,117,332 A | 9/2000 | Hatch et al. |
| 6,228,393 B1 | 5/2001 | DiCosmo et al. |
| 6,329,488 B1 | 12/2001 | Terry et al. |
| 6,350,738 B1 | 2/2002 | Savage et al. |
| 6,486,148 B2 | 11/2002 | Savage et al. |
| 6,562,318 B1 | 5/2003 | Filler |
| 6,582,713 B2 | 6/2003 | Newell et al. |
| 6,673,771 B1 | 1/2004 | Greene et al. |
| 6,767,904 B2 | 7/2004 | Savage et al. |
| 6,803,066 B2 | 10/2004 | Traeder |
| 6,872,303 B2 | 3/2005 | Knapp et al. |
| 6,939,376 B2 | 7/2005 | Shulze et al. |
| 7,282,214 B2 | 10/2007 | Wilcox et al. |
| 7,381,439 B2 | 6/2008 | Hilgren et al. |
| 7,598,234 B2 | 10/2009 | Savage et al. |
| 7,659,061 B2 | 2/2010 | Hendl et al. |
| 7,754,705 B2 | 7/2010 | Savage et al. |
| 7,854,941 B2 | 12/2010 | Urban et al. |
| 7,993,903 B2 | 8/2011 | Hayakawa et al. |
| 8,211,879 B2 | 7/2012 | Savage et al. |
| 8,529,681 B1 | 9/2013 | Hibbs et al. |
| 8,623,416 B2 | 1/2014 | Zasloff et al. |
| 8,691,252 B2 | 4/2014 | Savage |
| 8,784,857 B2 | 7/2014 | Savage |
| 8,932,614 B2 | 1/2015 | Savage et al. |
| 8,945,217 B2 | 2/2015 | Savage et al. |
| 8,975,310 B2 | 3/2015 | Savage |
| 9,155,746 B2 | 10/2015 | Genberg et al. |
| 9,161,942 B2 | 10/2015 | Genberg et al. |
| 9,314,472 B2 | 4/2016 | Beus et al. |
| 9,345,655 B2 | 5/2016 | Vazquez et al. |
| 9,387,215 B2 | 7/2016 | Beus et al. |
| 9,434,759 B1 | 9/2016 | Savage |
| 9,527,883 B2 | 12/2016 | Savage et al. |
| 9,533,063 B1 | 1/2017 | Savage |
| 9,546,195 B2 | 1/2017 | Savage |
| 9,603,859 B2 | 3/2017 | Genberg et al. |
| 2002/0091278 A1 | 7/2002 | Savage et al. |
| 2003/0018306 A1 | 1/2003 | Bucay-Couto et al. |
| 2003/0099717 A1 | 5/2003 | Cabrera |
| 2003/0170354 A1 | 9/2003 | Beelman et al. |
| 2004/0009227 A1 | 1/2004 | Yao |
| 2004/0011358 A1 | 1/2004 | Smaldone et al. |
| 2004/0018154 A1 | 1/2004 | Pan |
| 2004/0058974 A1 | 3/2004 | Courtney et al. |
| 2004/0071781 A1 | 4/2004 | Chattopadhyay et al. |

(Continued)

FOREIGN PATENT DOCUMENTS

| | | |
|---|---|---|
| CN | 101378761 | 3/2009 |
| CN | 102172356 | 9/2011 |

(Continued)

OTHER PUBLICATIONS

U.S. Appl. No. 15/926,534, filed Mar. 20, 2018, Savage.

(Continued)

Primary Examiner — San Ming R Hui
(74) Attorney, Agent, or Firm — Workman Nydegger

(57) ABSTRACT

Disclosed herein are methods of treating cancer and/or reducing cellular proliferation in a patient, comprising identifying a patient in need of treatment and administering a therapeutically effective amount of at least one cationic steroid antimicrobial (CSA), or a pharmaceutically acceptable salt thereof. Kits comprising such compositions and instructions on such methods are also contemplated herein.

20 Claims, No Drawings

(56) References Cited

U.S. PATENT DOCUMENTS

| | | |
|---|---|---|
| 2004/0126409 A1 | 7/2004 | Wilcox et al. |
| 2004/0170563 A1 | 9/2004 | Meade |
| 2004/0259445 A1 | 12/2004 | Hilfenhaus et al. |
| 2005/0032765 A1 | 2/2005 | Savage et al. |
| 2005/0075321 A1 | 4/2005 | Ahlem et al. |
| 2005/0244468 A1 | 11/2005 | Huang et al. |
| 2005/0267051 A1 | 12/2005 | Lee et al. |
| 2006/0062742 A1 | 3/2006 | Davis et al. |
| 2006/0269485 A1 | 11/2006 | Friedman et al. |
| 2007/0053788 A1 | 3/2007 | Zhao |
| 2007/0077292 A1 | 4/2007 | Pinsky |
| 2007/0106393 A1 | 5/2007 | Miles et al. |
| 2007/0134292 A1 | 6/2007 | Suokas et al. |
| 2007/0154554 A1 | 7/2007 | Burgermeister et al. |
| 2007/0190066 A1 | 8/2007 | Savage et al. |
| 2007/0190067 A1* | 8/2007 | Savage ................ A61K 31/56 424/160.1 |
| 2007/0190558 A1 | 8/2007 | Savage et al. |
| 2008/0124376 A1 | 5/2008 | Pruitt et al. |
| 2008/0174035 A1 | 7/2008 | Winterton |
| 2008/0188819 A1 | 8/2008 | Kloke et al. |
| 2008/0279944 A1 | 11/2008 | Sawhney |
| 2009/0016973 A1 | 1/2009 | Ratcliff et al. |
| 2009/0054295 A1 | 2/2009 | Vicari et al. |
| 2009/0068122 A1 | 3/2009 | Pilch et al. |
| 2009/0099531 A1 | 4/2009 | Griesbach, III |
| 2009/0252781 A1 | 10/2009 | Sawhney et al. |
| 2009/0324517 A1 | 12/2009 | Kline |
| 2010/0022481 A1 | 1/2010 | Wang et al. |
| 2010/0092398 A1 | 4/2010 | Reynolds |
| 2010/0226884 A1 | 9/2010 | Chang et al. |
| 2010/0310478 A1 | 12/2010 | Fitzgerald et al. |
| 2010/0330086 A1 | 12/2010 | Savage et al. |
| 2011/0091376 A1 | 4/2011 | Savage |
| 2011/0123624 A1 | 5/2011 | Zasloff |
| 2011/0135742 A1 | 6/2011 | Kim et al. |
| 2011/0230589 A1 | 9/2011 | Maggio et al. |
| 2012/0088733 A1 | 4/2012 | Kim et al. |
| 2012/0128793 A1 | 5/2012 | Miller et al. |
| 2013/0004586 A1 | 1/2013 | Vachon |
| 2013/0022651 A1 | 1/2013 | Savage |
| 2013/0040265 A1 | 2/2013 | Park et al. |
| 2013/0236619 A1 | 9/2013 | Savage |
| 2013/0280312 A1 | 10/2013 | De Szalay |
| 2013/0280391 A1 | 10/2013 | Savage |
| 2014/0219914 A1 | 8/2014 | Govindan et al. |
| 2014/0271761 A1 | 9/2014 | Savage et al. |
| 2014/0274913 A1 | 9/2014 | Savage et al. |
| 2014/0336131 A1 | 11/2014 | Savage et al. |
| 2014/0363780 A1 | 12/2014 | Vazquez et al. |
| 2015/0093423 A1 | 4/2015 | Savage et al. |
| 2015/0110767 A1 | 4/2015 | Savage et al. |
| 2015/0314342 A1 | 4/2015 | Beus et al. |
| 2015/0374719 A1 | 6/2015 | Genberg et al. |
| 2015/0203527 A1 | 7/2015 | Savage |
| 2015/0239928 A1 | 8/2015 | Savage |
| 2015/0258121 A1 | 9/2015 | Darien et al. |
| 2015/0258122 A1 | 9/2015 | Beus et al. |
| 2015/0258123 A1 | 9/2015 | Savage et al. |
| 2015/0366880 A1 | 9/2015 | Genberg et al. |
| 2016/0193232 A1 | 3/2016 | Beus et al. |
| 2016/0199390 A1 | 3/2016 | Beus et al. |
| 2016/0052959 A1 | 8/2016 | Savage |
| 2016/0022702 A1 | 10/2016 | Savage et al. |
| 2016/0045421 A1 | 10/2016 | Vazquez et al. |
| 2016/0096864 A1 | 10/2016 | Savage |
| 2016/0311850 A1 | 10/2016 | Savage et al. |
| 2016/0311851 A1 | 10/2016 | Savage et al. |
| 2017/0035677 A1 | 2/2017 | Vazquez et al. |
| 2017/0080128 A1 | 3/2017 | Genberg et al. |
| 2017/0137459 A1 | 5/2017 | Savage |
| 2017/0210776 A1 | 7/2017 | Savage |
| 2017/0232004 A1 | 8/2017 | Savage et al. |
| 2017/0258963 A1 | 9/2017 | Savage et al. |

FOREIGN PATENT DOCUMENTS

| | | |
|---|---|---|
| DE | 1037074 | 8/1958 |
| EP | 0341951 | 11/1989 |
| EP | 1208844 | 5/2002 |
| EP | 1219631 | 7/2002 |
| JP | 02014741 | 1/1990 |
| JP | H0474026 | 11/1992 |
| JP | 06153779 | 6/1994 |
| JP | 07501826 | 2/1995 |
| JP | 09248454 | 9/1997 |
| JP | 2002505292 | 2/2002 |
| JP | 2002255771 | 9/2002 |
| JP | 2002534532 | 10/2002 |
| JP | 2002538093 | 11/2002 |
| JP | 2004506645 | 3/2004 |
| JP | 2010533051 | 10/2010 |
| JP | 2010538074 | 12/2010 |
| JP | 2011527702 | 11/2011 |
| JP | 2014500741 | 1/2014 |
| WO | 1995024415 | 9/1995 |
| WO | 9827106 | 6/1998 |
| WO | 1999044616 | 9/1999 |
| WO | 2000042058 | 7/2000 |
| WO | 2002014342 | 2/2002 |
| WO | 2002067979 | 9/2002 |
| WO | 2003015757 | 2/2003 |
| WO | 03090799 | 11/2003 |
| WO | 2004082588 | 9/2004 |
| WO | 2004112852 | 12/2004 |
| WO | 2007089903 | 8/2007 |
| WO | 2007089906 | 8/2007 |
| WO | 2007089907 | 8/2007 |
| WO | 2007134176 | 11/2007 |
| WO | 2008038965 | 4/2008 |
| WO | 2008048340 | 4/2008 |
| WO | 2009079066 | 6/2009 |
| WO | 2009144708 | 12/2009 |
| WO | 2010006192 | 1/2010 |
| WO | 2010036427 | 4/2010 |
| WO | 2010062562 | 6/2010 |
| WO | 2011066260 | 6/2011 |
| WO | 2011109704 | 9/2011 |
| WO | 2012061651 | 5/2012 |
| WO | 2013029055 | 2/2013 |
| WO | 2013029059 | 2/2013 |
| WO | 2013040269 | 3/2013 |
| WO | 2013109236 | 7/2013 |
| WO | 2013167743 | 11/2013 |
| WO | 2014062960 | 4/2014 |

OTHER PUBLICATIONS

U.S. Appl. No. 15/926,577, filed Mar. 20, 2018, Savage et al.
U.S. Appl. No. 15/934,534, filed Mar. 23, 2018, Savage.
Alafort et al., "Lys and Arg in UBI: A specific site for a stable Tc-99m complex?", Nuclear Medicine and Biology 30 (2003) 605-615.
Alhanout K et al: "Squalamine as an example of a new potent antimicrobial agents class: a critical review.", Current Medicinal Chemistry 2010, vol. 17, No. 32, 2010, pp. 3909-3917.
Atiq-Ur-Rehman Li C et al: "Preparation of Amino Acid-Appended Cholic Acid Derivatives as Sensitizers of Gram-Negative Bacteria", Tetrahedron Letters, Elsevier, Amsterdam, NL, vol. 40, No. 10, Mar. 5, 1999 (Mar. 5, 1999), pp. 1865-1868, XP004155984, ISSN: 0040-4039, DOI: 10.1016/S0040-4039(99)00075-1.
BASF, Pluronic® Block Copolymer NF Grades (Poloxamer NF Grades), Technical Bulletive (2004).
Bakri et al., "Inhibitory effect of garlic extract on oral bacteria", Archives of Oral Biology, 50: 645-651.
Bellini et al., "Cholic and deoxycholic acids derivatives (Part I). Antimicrobial activity of cholane compounds", European J. of Medicinal Chem., 18(2), pp. 185-190, 1983.
Belikov V.G., Pharmaceutical Chemistry, M., Higher School, 1993, p. 43-47.
Bellini et al., "Cholic and deoxycholic acids derivatives (Part II). Antimicrobial activity of cholane compounds", European J. of Medicinal Chem., 18(2), pp. 191-195, 1983.

(56) References Cited

OTHER PUBLICATIONS

Berge et al., "Pharmaceutical Salts", Journal of Pharmaceutical Sciences, Jan. 1977, vol. 66, No. 1, pp. 1-19.
Bridot et al., "Hybrid Gadolinium Oxide Nanoparticles: Multimodal Contrast Agents for in Vivo Imaging", Journal of American Chemical Society, vol. 129, No. 16, pp. 5076-5084, Mar. 31, 2007.
Britton et al, "Imaging bacterial infection with 99mTc-ciprofloxacin (Infection)", Journal of Clinical Pathology, vol. 55, pp. 817-823, Apr. 6, 2015.
Brown, "Bioisosteres in Medicinal Chemistry, First Edition", edited by Nathan Brown, 2012, Ch. 2 Classical Bioisosteres, pp. 1-52.
Bucki et al., "Salivary mucins inhibit antibacterial activity of the cathelicidin-derived LL-37 peptide but not the cationic steroid CSA-13", Journal of Antimicrobial Chemotherapy (2008) 62: 329-335, 7 pages.
Bucki et al., "Resistance of the antibacterial agent ceragenin CSA-13 to inactivation by DNA or F-actin and its activity in cystic fibrosis sputum", Journal of Antimicrobial Chemotherapy (2007) 60: 535-545, 11 pages.
Bush, "*Staphylococcal* Infections", Merck Manuals Professional Edition, http://www.merckmanuals.com/professional/infectious-diseases/gram-positive-cocci/staphylococcal-infections.
Chin et al, "Antimicrobial Activities of Ceragenins against Clinical Isolates of Resistant *Staphylococcus aureas*.", Antimicrobial Agents and Chemotherapy, vol. 51, No. 4, Apr. 2007, p. 1268-1273.
Cipolla et al., "Inhaled antibiotics to treat lung infection", Pharm Pat Anal., Sep. 2013.
Clara et al., "Preclinical evaluation of magainin-A as a contraceptive antimicrobial agent", Fertility and Sterility 81 (5), pp. 1357-1365, 2004.
De Cuyper et al., "Surface functionalization of magnetoliposomes in view of improving iron oxide-based magnetic resonance imaging contrast agents: Anchoring of gadolinium ions to a lipophilic chelate", 2007 Anal. Biochem. 367: 266-273. Published online May 10, 2007.
Dennison et al., "Anticancer α-Helical Peptides and Structure/Function Relationships Underpinning their Interactions with Tumour Cell Membranes", Current Protein and Peptide Science, 2006, 7, No. 6, pp. 1-13.
Derakhshandeh et al., "Thermosensitive Pluronic hydrogel: prolonged injectable formulation for drug abuse", Drug Design, Development and Therapy, 2010, 255-262.
Ding, et al., "Origins of cell selectivity of cationic steroid antibiotics", Journal of American Chemical Society, Oct. 2004, pp. 13642-13648.
Dörwald, "Side Reactions in Organic Synthesis", 2005, Wiley-VCH Verlag GmbH & Co., KGaA, Weinhelm, Preface. p. IX.
Elder et al., "The Utility of Sulfonate Salts in Drug Development", Journal of Pharmaceutical Sciences 99(7): 2948-2961.
Epand et al., "Bacterial lipid composition and the antimicrobial efficacy of cationic steroid compounds (Ceragenins)", BBA, 2007, pp. 65-78.
Erskine et al., "Mastitis in Cattle", Merck Manual: Veterinary Manual. Electronic Resource: [http://www.merckvetmanual.com/reproductive-system/mastitis-in-large-animals/mastitis-in-cattle], retrieved Mar. 8, 2017.
Fichna et al., "Synthesis of Target-Specific Radiolabeled Peptides for Diagnostic Imaging", Bioconjugate Chem., 2003, 14, 3-17, American Chemical Society.
Food definition, Merriam Webster, https://www.merriam-webster.com/dictionary/food, Accessed Feb. 12, 2018.
Fritsch et al, "In Vitro Activity of Nine Developmental Cationic Steroid Compounds (Ceragenins) against Clinical Isolates of Clostridium difficile", The 46th Interscience Conference on Antimicrobial Agents and Chemotherapy, Sep. 27, 2006, pp. 1-1.
Guan et al: "Preparation and Characterization of Cholic Acid-Derived Antimicrobial Agents with Controlled Stabilities", Organic Letters, American Chemical Society, US, vol. 2, No. 18, Sep. 7, 2000 (Sep. 7, 2000), pp. 2837-2840.
Guan et al: "Supporting Information: Preparation and Characterization of Cholic Acid-Derived Antimicrobial Agents with Controlled Stabilities", Organic Letters, Aug. 17, 2000 (Aug. 17, 2000), pp. 1-7, XP55017313, Retrieved from the Internet: URL:http://pubs.acs.org/doi/suppl/10.1021/ol0062704/suppl file/ol0062704 sl.pdf.
Howell, et al., "Ceragenins: A 1-18, class of Antiviral Compounds to Treat Orthopox Infections", Journal of Investigative Dermatology, vol. 129, No. 11, Jun. 11, 2009, pp. 2688-2675.
Huang L. et al.: "Synthesis and characterization of organometallic rhenium(I) and technetium(I) bile acid complexes" Journal of organometallic chemistry, Elsevier-Sequoia S.A. Lausanne, CH, col. 694, No. 20, Sep. 15, 2009, pp. 3247-3253.
International Search Report for PCT Application No. PCT/US2009/047485 dated Feb. 17, 2010.
International Search Report for PCT Application No. PCT/US2011/059225 dated Jan. 31, 2012.
International Search Report for PCT Application No. PCT/US2012/047750, dated Oct. 5, 2012, Filed Date: Sep. 27, 2012, 3 pages.
International Search Report for PCT Application No. PCT/US2012/055244 dated Dec. 5, 2012.
International Search Report for PCT Application No. PCT/US2012/055248 dated Feb. 14, 2013.
International Search Report for PCT Application No. PCT/US2013/038090, dated Jul. 24, 2013.
International Search Report for PCT Application No. PCT/US2014/034986 dated Aug. 28, 2014.
International Search Report for PCT Application No. PCT/US2013/065510, dated Apr. 30, 2015.
International Search Report for PCT Application No. PCT/US2015/020166 dated Sep. 2, 2015.
International Search Report for PCT Application No. PCT/US2015/038029 dated Sep. 29, 2015.
International Search Report for PCT Application No. PCT/US2015/046412 dated Dec. 1, 2015.
International Search Report for PCT Application No. PCT/US2015/054434 dated Dec. 23, 2015.
International Search Report for PCT Application No. PCT/US2016/052771 dated Dec. 9, 2016.
Isogai E et al: "Ceragenin CSA-13 exhibits antimicrobial activity against cariogenic and periodontopathic bacteria", Oral Microbiology and Immunology, vol. 24, No. 2, Apr. 2009 (Apr. 2009), pp. 170-172.
Iuliano, "Synthesis of four cholic acid-based CSPs containing 2-naphthyl carbamate and 3,5-dinitrophenylcarbamate moieties and their evaluation in the HPLC resolution of racemic compounds", Tetrahedron: Asymmetry 13 (2002) 1265-1275.
Jones et al, "Physicochemical Characterization of Hexetidine-Impregnated Endotracheal Tube Poly(Vinyl Chloride) and Resistance to Adherence of Respiratory Bacterial Pathogens", Pharmaceutical Research 19(6): 818-824.
Journal of Ocular Pharmacology and Therapeutics, vol. 27, Issue 1, Table of Contents (Mary Ann Liebert, Inc. publishers), Retrieved from internet <URL:http://online.libertpub.com/toc/jop/27/1>, Downloaded Dec. 1, 2017, 5 pages.
Lai et al- "Controlled Released of a Bactericidal Ceragenin-Polymer Conjugate", Sep. 227, 2006, p. 1, 46th Annual Interscience Conference on Antimicrobial Agents and Chemotherapy.
Lankinen et al., "Ga-Dota-Peptide Targeting VAP-1 for in Vivo Evaluation of Inflammatory and Infectious Bone Conditions", 52nd Annual Meeting of the Orthopaedic Research Society.
K. Leszczynska et al., "Antibacterial activity of the human host defence peptide LL-37 and selected synthetic cationic lipids against bacteria associated with oral and upper respiratory tract infections", Journal of Antimicrobial Chemotherapy Advance Access, Published Nov. 7, 2012.
K. Leszczynska et al., "Potential of ceragenin CSA-13 and its mixture with pluronic F-127 as treatment of topical bacterial infections", Journal of Applied Microbiology, vol. 110, No. 1, Oct. 21, 2010, pp. 229-238.
Li et al., "Antimicrobial Activities of Amine- and Guanidine-functionalized Cholic Acid Derivatives", Antimicrobial Agents and Chemotherapy, American Society for Microbiology, Washington DC, US, vol. 43, No. 6, Jun. 1999, pp. 1347-1349.

(56) References Cited

OTHER PUBLICATIONS

Li et al., "Incremental conversion of Outer-Membrane Permeabilizers into Potent Antibiotics for Gram-Negative Bacteria", J. Am. Chem. Soc. 1999, 121, 931-940.

Louw et al., "Recueil des Travaux Chimiques des Pays-Bas et la Belgique", vol. 73, pp. 667-676, 1954.

Lowe et al., "Effect of Hydrophobicity of a Drug on its Release from Hydrogels with Different Topological Structures" Journal of Polymer Science (1999) 73: 1031-1039 (9 pages).

Martin, L., WebMD, 2012, pp. 1-25.

Massoud et al., "Molecular imaging in living subjects: seeing fundamental biological processes in a new light", Genes & Development 17: 545-580 2003, Cold Spring Harbor Laboratory Press.

Muñoz-Juárez et al., "Wide-Lumen Stapled Anastomosis vs. Conventional End-to-End Anastomosis in the Treatment of Crohn's Disease", Dis Colon Rectum 2001; 44: No. 1, 20-26).

Novy et al., "Infections as a Cuase of Infertility", Glob. Libr. Women's med., (ISSN: 1756-2228) 2008; DOI 10.3843/GLOWM.10328.

Papo et al., "Host peptides as new weapons in cancer treatment", CMLS Cell. Mol. Life Sci. 62 (2005), 784-790.

Emily L. Perry et al., "Assessing peri-implant tissue infection prevention in a percutaneous model", Journal of Biomedical Materials Research Part B: Applied Biomaterials, vol. 02B, Nov. 19, 2009, pp. 397-408.

Piktel et al. Sporicidal Activity of Ceragenin CSA-13 Against Bacillus Subtillis, Scientific Reports, vol. 7, Mar. 15, 2017 [retrieved on Apr. 24, 2018. Retreived from the internet: <URL: https://www.nature.com/articles/srep44452.pdf> Entire Document.

Pitten F-A, et al., "Efficacy of cetylpyridinium chloride used as oropharyngeal antiseptic" Arzenimittel Forschung. Rug Research, ECV Editio Cantor Verlag, Aulendorf, DE, vol. 51, No. 7, Jan. 1, 2001, pp. 588-595.

Polat et al., "In Vitro Amoebicidal Activity of a Ceragenin, Cationic Steroid Antibiotic-13, Against Acanthamoeba castellanii and Its Cytotoxic Potential", Journal of Ocular Pharmacology and Therapeutics, vol. 27, No. 1, 2011.

Press release (Ceragenix Pharmaceuticals, Wayne State University, Brigham Young University, Systemic Anti-Infectives, Preclinical Title—Ceragenin™ Compound demonstrates potent activity multidrug resistant bacterial strains of Pseudomonas, Denver, CO—Published Dec. 20, 2007).

Pycock, "The Dirty Mare", https://www.equine-reproduction.com/articles/DirtyMare.shtml, 2003.

Roohi et al., Prepration, quality control and biological evaluation of 99m-Tc-labelled cationic steroid antibiotic (CSA-13), Radiochim. Acta 197, 57-62 (2009).

Savage, et al., "Antibacterial Activities of Thin Films Containing Ceragenins", Microbial Surfaces: Structure, Interactions and Reactivity, ACS, May 30, 2008, pp. 65-78.

Paul B. Savage, et al: "Antibacterial Properties of cationic steroid antibiotics", FEMS Microbiology Letters, vol. 217, Nov. 2002, pp. 1-7.

P. B. Savage, et al., "Thin Films Containing Ceragenins Prevent Biofilm Formation on Endotracheal Tubes", 9th International Federation of Infection Control Congress, Oct. 14, 2008, pp. 1-1.

P. B. Savage, et al., "Use of a Ceragenin-Based Coating to Prevent Bacterial Colonization of Urinary Catheters", 48th Annual Interscience Conference on Anti-Microbial Agents & Chemotherapy, Oct. 26, 2008, pp. 1-1.

Schmidmaier et al., "Local Application of Growth Factors (Insulin-Like Growth Factor-1 and Transforming Growth Factor-β1) From a Biodegradable Poly(D, L-lactide) Coating of Osteosynthetic Implants Accelerates Fracture Healing in Rats", Bone vol. 28 No. 4, Apr. 2001.

Shi et al., "Multi-center randomized double-blind clinical trial on efficacy of a mouthwash containing 0.1% cetylpiridinium chloride on gingivitis and plaque and its safety", Chinese Journal of Evidence-Based Medicine (Sep. 2003, vol. 3, No. 3, pp. 171-177).

K.D. Sinclair, et al., "Development of a broad spectrum polymer-released antimicrobial coating for the prevention of resistant strain bacterial infections", Journal of Biomedical Materials Research Part A, vol. 100A, No. 10, May 24, 2012, pp. 2732-2738.

Steeneveld, et al., "Cow-specific treatment of clinical mastitis: an economic approach", Journal of Dairy Science vol. 94, Jan. 2011, pp. 174-188.

Survey Research on Behcet's Disease, 2005 to 2007 Comprehensive Survey Reports, 2008, pp. 34-39.

Suzuki et al., "Molecular Genetics of Plant Sterol Backbone Synthesis", 2007; Lipids; 42: 47-54.

Van Bambeke et al: "The bacterial envelope as a target for novel anti-MRSA antibiotics", Trends in Pharmacological Sciences, Elsevier, Haywarth, GB, vol. 29, No. 3, Feb. 11, 2008 (Feb. 11, 2008), pp. 124-134.

Van Den Bogaard et al., "Antibiotic Usage in Animals: Impact on Bacterial Resistance and Public Health"; 1999; Drugs; 58 (4): 589-607.

Welling et al., "Radiochemical and biological characteristics of 99m-Tc-UBI 29-41 for imaging of bacterial infections", Nuclear Medicine and Biology 29 (2002) 413-422.

Willemen et al., "Miceli Formation and Antimicrobial Acivity of Cholic Acid Derivatives with three Permanent Ionic Head Groups", Angew. Chem. Int. Ed., 2002, 41, No. 22.

Williams et al., "In vivo efficacy of a silicone-cationic steroid antimicrobial coating to prevent implant-related infection", Biomaterials, Nov. 2012: 33(33): 8641-8656 (Department of Brigham Young University).

Winter et al., "Improved paragmentic chelate for molecular imaging with MRI", 2005 J. Magn. Magn. Mater. 293: 540-545.

Wu et al., "Biodegradable hydrophobic-hydrophilic hybrid hydrogels: swelling behavior and controlled drug release", Journal of Biomaterials Science Polymer Edition (J. Biomatter. Sci. Polymer Ed.) (2008) 19 (4): 411-429 (20 pages, including copyright information).

Xin-Zhong Lai, et al., "Ceragenins: Cholic Acid-Based Mimics of Antimicrobial peptides", Account of Chemical Research vol. 41, No. 10, Oct. 21, 2008, pp. 1233-1240.

Melinda Yin, et al., "Antiangiogenic Treatment Delays Chondrocyte Maturation and Cone Formation During Lim Skeletogenesis", Journal of Vone and Mineral Research, American Society for Bone and Mineral Research, New York, NY, US, vol. 17, No. 1, Jan. 1, 2002.

Zanger et al., "Structure-Activity Relationship and Drug Design", Remington's Pharmaceutical Sciences, Chapter 27, 16th Edition, 1980, pp. 420-425.

\* cited by examiner

METHODS FOR REDUCING CELLULAR PROLIFERATION AND TREATING CERTAIN DISEASES

CROSS-REFERENCE TO RELATED APPLICATIONS

This application is a continuation of U.S. patent application Ser. No. 14/149,675, filed Jan. 7, 2014, which claims benefit of U.S. Provisional Application No. 61/749,800, filed Jan. 7, 2013, the disclosures of which are incorporated herein by reference in their entirety.

BACKGROUND

Field

Cationic steroid antimicrobials ("CSAs") for treating certain diseases such as cancer and/or reducing cellular proliferation.

Description of the Related Art

Cancer is a term used for diseases in which abnormal cells divide without control and may invade other tissues. Cancer cells may also spread to other parts of the body through the blood and lymph systems.

There are more than 100 different types of cancer, with most cancers named for the organ or type of cell in which they start. For example, cancer that begins in the colon may be referred to as colon cancer; cancer that begins in basal cells of the skin may be referred to as basal cell carcinoma. Common types of cancer in the United States are Bladder Cancer, Lung Cancer, Breast Cancer, Melanoma, Colon and Rectal Cancer, Non-Hodgkin Lymphoma, Endometrial Cancer, Pancreatic Cancer, Kidney (Renal Cell) Cancer, Prostate Cancer, Leukemia, and thyroid Cancer.

Cancer types can also be grouped into broader categories. The main categories of cancer include: carcinoma—cancer that begins in the skin or in tissues that line or cover internal organs; sarcoma—cancer that begins in bone, cartilage, fat, muscle, blood vessels, or other connective or supportive tissue; leukemia—cancer that starts in blood-forming tissue such as the bone marrow and causes large numbers of abnormal blood cells to be produced and enter the blood; lymphoma and myeloma—cancers that begin in the cells of the immune system; central nervous system cancers—cancers that begin in the tissues of the brain and spinal cord.

Several techniques for treating cancer are known in the art. Such techniques include chemotherapy, radiation therapy, surgery, and transplantation. Each of these techniques, however, have undesirable side effects and varying success rates. Indeed, U.S. statistics for 2012 indicate that there will be an estimated 1,638,910 new cases of cancer (not including non-melanoma skin cancers) and 577,190 estimated deaths from cancer. Therefore, a need exists to develop new methods for treating cancer and/or diseases associated with cellular proliferation.

SUMMARY

Disclosed herein are methods of treating cancer and/or reducing cellular proliferation in a patient, comprising identifying a patient in need of treatment and administering a therapeutically effective amount of at least one cationic steroid antimicrobial (CSA), or a pharmaceutically acceptable salt thereof. We have discovered that CSAs have anti-proliferative activity against a wide variety of cell lines, including known cancerous cell lines, and have demonstrated both anti-proliferative and cytotoxic activities. Kits comprising such compositions and instructions on such methods are also contemplated herein.

In some embodiments, the cancer is leukemia, non-small cell lung cancer, colon cancer, CNS cancer, skin cancer, ovarian cancer, renal cancer, prostate cancer, breast cancer, or multiple myeloma. In some embodiments, the cancer is leukemia, non-small cell lung cancer, colon cancer, CNS cancer, melanoma, ovarian cancer, renal cancer, prostate cancer, or breast cancer.

In other embodiments, the method reduces the proliferation of cells and/or cell lines by contacting a CSA with a cell and/or cell line such as CCRF-CEM; HL-60(TB); K-562; MOLT-4; RPMI-8226; SR; A549/ATCC; EKVX; HOP-62; HOP-92; NCI-H226; NCI-H23; NCI-H322M; NCI-H460; NCI-H522; COLO 205; HCC-2998; HCT-116; HCT-15; HT29; KM12; SW-620; SF-268; SF-295; SF-539; SNB-19; SNB-75; U251; LOX IMVI; MALME-3M; M14; SK-MEL-2; SK-MEL-28; SK-MEL-5; UACC-257; UACC-62; IGROV1; OVCAR-3; OVCAR-4; OVCAR-5; OVCAR-8; NCI/ADR-RES; SK-OV-3; 786-0; A4981; ACHN; CAKI-1; RXF 393; SN12C; TK-10; UO-31; PC-3; DU-145; MCF7; NCI-ADR-RES; MDA-MB-231/ATCC; HS 578T; MDA-MB-435; MDA-MB-468; BT-549; or T-47D. An embodiment also includes contacting cells of a patient with a CSA wherein the cells are cancer cells of the type represented by the foregoing cell lines.

In some embodiments, the CSA is a compound of Formula (I) or a pharmaceutically acceptable salt thereof:

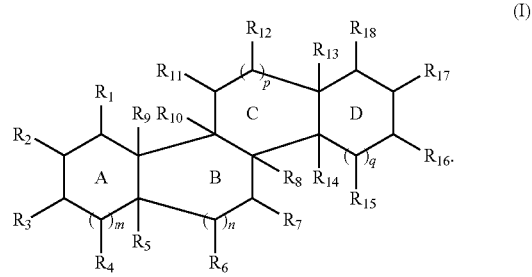

(I)

In some embodiments, the CSA, or a pharmaceutically acceptable salt thereof, is selected from the compound of Formula (II):

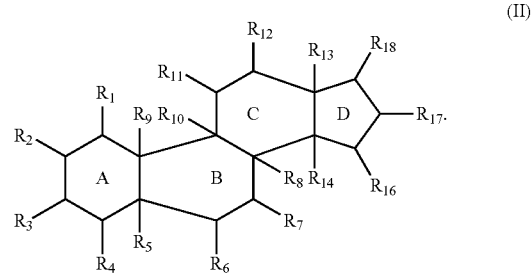

(II)

In some embodiments, the CSA, or a pharmaceutically acceptable salt thereof, is selected from the compound of Formula (III):

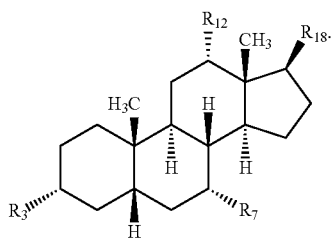

(Ia)

In some embodiments rings A, B, C, and D are independently saturated, or are fully or partially unsaturated, provided that at least two of rings A, B, C, and D are saturated; m, n, p, and q are independently 0 or 1; $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted alkyl, a substituted or unsubstituted hydroxyalkyl, a substituted or unsubstituted alkyloxyalkyl, a substituted or unsubstituted alkylcarboxyalkyl, a substituted or unsubstituted alkylaminoalkyl, a substituted or unsubstituted alkylaminoalkylamino, a substituted or unsubstituted alkylaminoalkylaminoalkylamino, a substituted or unsubstituted aminoalkyl, a substituted or unsubstituted aryl, a substituted or unsubstituted arylaminoalkyl, a substituted or unsubstituted haloalkyl, a substituted or unsubstituted alkenyl, a substituted or unsubstituted alkynyl, oxo, a linking group attached to a second steroid, a substituted or unsubstituted aminoalkyloxy, a substituted or unsubstituted aminoalkyloxyalkyl, a substituted or unsubstituted aminoalkylcarboxy, a substituted or unsubstituted aminoalkylaminocarbonyl, a substituted or unsubstituted aminoalkylcarboxamido, a substituted or unsubstituted di(alkyl)aminoalkyl, $H_2N$—$HC(Q_5)$-$C(O)$—$O$—, $H_2N$—$HC(Q_5)$-$C(O)$—$N(H)$—, a substituted or unsubstituted azidoalkyloxy, a substituted or unsubstituted cyanoalkyloxy, P.G.-HN—HC($Q_5$)-C(O)—O—, a substituted or unsubstituted guanidinoalkyloxy, a substituted or unsubstituted quaternary ammonium alkylcarboxy, and a substituted or unsubstituted guanidinoalkyl carboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted alkyl, a substituted or unsubstituted hydroxyalkyl, a substituted or unsubstituted alkyloxyalkyl, a substituted or unsubstituted aminoalkyl, a substituted or unsubstituted aryl, a substituted or unsubstituted haloalkyl, a substituted or unsubstituted alkenyl, a substituted or unsubstituted alkynyl, oxo, a linking group attached to a second steroid, a substituted or unsubstituted aminoalkyloxy, a substituted or unsubstituted aminoalkylcarboxy, a substituted or unsubstituted aminoalkylaminocarbonyl, a substituted or unsubstituted di(alkyl)aminoalkyl, $H_2N$—$HC(Q_5)$-$C(O)$—$O$—, $H_2N$—$HC(Q_5)$-$C(O)$—$N(H)$—, azidoalkyloxy, cyanoalkyloxy, P.G.-HN—HC($Q_5$)-C(O)—O—, guanidinoalkyloxy, and guanidinoalkylcarboxy, where $Q_5$ is a side chain of any amino acid, P.G. is an amino protecting group, provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted aminoalkyl, a substituted or unsubstituted aminoalkyloxy, a substituted or unsubstituted alkylcarboxyalkyl, a substituted or unsubstituted alkylaminoalkylamino, a substituted or unsubstituted alkylaminoalkylaminoalkylamino, a substituted or unsubstituted aminoalkylcarboxy, a substituted or unsubstituted arylaminoalkyl, a substituted or unsubstituted aminoalkyloxyaminoalkylaminocarbonyl, a substituted or unsubstituted aminoalkylaminocarbonyl, a substituted or unsubstituted aminoalkylcarboxyamido, a quaternary ammonium alkylcarboxy, a substituted or unsubstituted di(alkyl)aminoalkyl, $H_2N$—$HC(Q_5)$-$C(O)$—$O$—, $H_2N$—$HC(Q_5)$-$C(O)$—$N(H)$—, azidoalkyloxy, cyanoalkyloxy, P.G.-HN—HC(Q5)-C(O)—O—, a substituted or unsubstituted guanidinoalkyloxy, and a substituted or unsubstituted guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted $(C_1$-$C_{18})$ alkyl, a substituted or unsubstituted $(C_1$-$C_{18})$ hydroxyalkyl, a substituted or unsubstituted $(C_1$-$C_{18})$ alkyloxy-$(C_1$-$C_{18})$ alkyl, a substituted or unsubstituted $(C_1$-$C_{18})$ alkylcarboxy-$(C_1$-$C_{18})$ alkyl, a substituted or unsubstituted $(C_1$-$C_{18})$ alkylamino-$(C_1$-$C_{18})$alkyl, a substituted or unsubstituted $(C_1$-$C_{18})$ alkylamino-$(C_1$-$C_{18})$ alkylamino, a substituted or unsubstituted $(C_1$-$C_{18})$ alkylamino-$(C_1$-$C_{18})$ alkylamino-$(C_1$-$C_{18})$ alkylamino, a substituted or unsubstituted $(C_1$-$C_{18})$ aminoalkyl, a substituted or unsubstituted aryl, a substituted or unsubstituted arylamino-$(C_1$-$C_{18})$ alkyl, a substituted or unsubstituted $(C_1$-$C_{18})$ haloalkyl, a substituted or unsubstituted $C_2$-$C_6$ alkenyl, a substituted or unsubstituted $C_2$-$C_6$ alkynyl, oxo, a linking group attached to a second steroid, a substituted or unsubstituted $(C_1$-$C_{18})$ aminoalkyloxy, a substituted or unsubstituted $(C_1$-$C_{18})$ aminoalkyloxy-$(C_1$-$C_{18})$ alkyl, a substituted or unsubstituted $(C_1$-$C_{18})$ aminoalkylcarboxy, a substituted or unsubstituted $(C_1$-$C_{18})$ aminoalkylaminocarbonyl, a substituted or unsubstituted $(C_1$-$C_{18})$ aminoalkylcarboxamido, a substituted or unsubstituted di($C_1$-$C_{18}$ alkyl)aminoalkyl, $H_2N$—$HC(Q_5)$-$C(O)$—$O$—, $H_2N$—$HC(Q_5)$-$C(O)$—$N(H)$—, a substituted or unsubstituted $(C_1$-$C_{18})$ azidoalkyloxy, a substituted or unsubstituted $(C_1$-$C_{18})$ cyanoalkyloxy, P.G.-HN—HC($Q_5$)-C(O)—O—, a substituted or unsubstituted $(C_1$-$C_{18})$ guanidinoalkyloxy, a substituted or unsubstituted $(C_1$-$C_{18})$ quaternary ammonium alkylcarboxy, and a substituted or unsubstituted $(C_1$-$C_{18})$ guanidinoalkyl carboxy, where $Q_5$ is a side chain of any amino acid (including a side chain of glycine, i.e., H), and P.G. is an amino protecting group; $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted $(C_1$-$C_{18})$ alkyl, a substituted or unsubstituted $(C_1$-$C_{18})$ hydroxyalkyl, a substituted or unsubstituted $(C_1$-$C_{18})$ alkyloxy-$(C_1$-$C_{18})$ alkyl, a substituted or unsubstituted $(C_1$-$C_{18})$ aminoalkyl, a substituted or unsubstituted aryl, a substituted or unsubstituted $(C_1$-$C_{18})$ haloalkyl, a substituted or unsubstituted $(C_2$-$C_6)$ alkenyl, a substituted or unsubstituted $(C_2$-$C_6)$ alkynyl, oxo, a linking group attached to a second steroid, a substituted or unsubstituted $(C_1$-$C_{18})$ aminoalkyloxy, a substituted or unsubstituted $(C_1$-$C_{18})$ aminoalkylcarboxy, a substituted or unsubstituted $(C_1$-$C_{18})$ aminoalkylaminocarbonyl, a substituted or unsubstituted di($C_1$-$C_{18}$ alkyl)aminoalkyl, $H_2N$—$HC(Q_5)$-$C(O)$—$O$—, $H_2N$—$HC(Q_5)$-$C(O)$—$N(H)$—, a substituted or unsubstituted $(C_1$-$C_{18})$ azidoalkyloxy, a substituted or unsubstituted $(C_1$-$C_{18})$ cyanoalkyloxy, P.G.-HN—HC($Q_5$)-C(O)—O—, a substituted or unsubstituted $(C_1$-$C_{18})$ guanidinoalkyloxy, and ($C_1$-$C_{18}$) guanidinoalkylcarboxy, where Q5 is a side chain of any amino acid, and P.G. is an amino protecting group; provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted ($C_1$-$C_{18}$) aminoalkyl, a substituted or unsubstituted ($C_1$-$C_{18}$) aminoalkyloxy, a substituted or unsubstituted ($C_1$-$C_{18}$) alkylcarboxy-($C_1$-$C_{18}$) alkyl, a substituted or unsubstituted ($C_1$-$C_{18}$) alkylamino-($C_1$-$C_{18}$) alkylamino, a substituted or unsubstituted ($C_1$-$C_{18}$) alkylamino-($C_1$-$C_{18}$) alkylamino ($C_1$-$C_{18}$) alkylamino, a substituted or unsubstituted ($C_1$-$C_{18}$) aminoalkylcarboxy, a substituted or unsubstituted arylamino ($C_1$-$C_{18}$) alkyl, a substituted or unsubstituted ($C_1$-$C_{18}$) aminoalkyloxy ($C_1$-$C_{18}$) aminoalkylaminocarbonyl, a substituted or unsubstituted ($C_1$-$C_{18}$) aminoalkylaminocarbonyl, a substituted or unsubstituted ($C_1$-$C_{18}$) aminoalkylcarboxamido, a substituted or unsubstituted ($C_1$-$C_{18}$) quaternary ammonium alkylcarboxy, a substituted or unsubstituted di($C_1$-$C_{18}$ alkyl)aminoalkyl, $H_2N$—HC($Q_5$)-C(O)—O—, $H_2N$—HC($Q_5$)-C(O)—N(H)—, a substituted or unsubstituted ($C_1$-$C_{18}$) azidoalkyloxy, a substituted or unsubstituted ($C_1$-$C_{18}$) cyanoalkyloxy, P.G.-HN—HC(Q5)-C(O)—O—, a substituted or unsubstituted ($C_1$-$C_{18}$) guanidinoalkyloxy, and a substituted or unsubstituted ($C_1$-$C_{18}$) guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy; $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$) alkyl, ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy; provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, unsubstituted ($C_1$-$C_{18}$) guanidinoalkyloxy, unsubstituted ($C_1$-Cis) quaternary ammonium alkylcarboxy, and unsubstituted ($C_1$-Cis) guanidinoalkyl carboxy.

In some embodiments, $R_3$, $R_7$, $R_{12}$, and $R_{18}$ are independently selected from the group consisting of hydrogen, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted arylamino-($C_1$-$C_{18}$) alkyl, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternary ammonium alkylcarboxy, and unsubstituted ($C_1$-Cis) guanidinoalkyl carboxy; and $R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and unsubstituted ($C_1$-$C_6$) alkyl.

In some embodiments, $R_3$, $R_7$, $R_{12}$, and $R_{18}$ are independently selected from the group consisting of hydrogen, an unsubstituted ($C_1$-$C_6$) alkyl, unsubstituted ($C_1$-$C_6$) hydroxyalkyl, unsubstituted ($C_1$-$C_{16}$) alkyloxy-($C_1$-$C_5$) alkyl, unsubstituted ($C_1$-$C_{16}$) alkylcarboxy-($C_1$-$C_5$) alkyl, unsubstituted ($C_1$-$C_{16}$) alkylamino-($C_1$-$C_5$)alkyl, ($C_1$-$C_{16}$) alkylamino-($C_1$-$C_5$) alkylamino, unsubstituted ($C_1$-$C_{16}$) alkylamino-($C_1$-$C_{16}$) alkylamino-($C_1$-$C_5$) alkylamino, an unsubstituted ($C_1$-$C_{16}$) aminoalkyl, an unsubstituted arylamino-($C_1$-$C_5$) alkyl, an unsubstituted ($C_1$-$C_5$) aminoalkyloxy, an unsubstituted ($C_1$-$C_{16}$) aminoalkyloxy-($C_1$-$C_5$) alkyl, an unsubstituted ($C_1$-$C_5$) aminoalkylcarboxy, an unsubstituted ($C_1$-$C_5$) aminoalkylaminocarbonyl, an unsubstituted ($C_1$-$C_5$) aminoalkylcarboxamido, an unsubstituted di($C_1$-$C_5$ alkyl)amino-($C_1$-$C_5$) alkyl, unsubstituted ($C_1$-$C_5$) guanidinoalkyloxy, unsubstituted ($C_1$-$C_{16}$) quaternary ammonium alkylcarboxy, and unsubstituted ($C_1$-$C_{16}$) guanidinoalkylcarboxy;

In some embodiments, $R_1$, $R_2$, $R_4$, $R_5$, $R_6$, $R_8$, $R_{10}$, $R_{11}$, $R_{14}$, $R_{16}$, and $R_{17}$ are each hydrogen; and $R_9$ and $R_{13}$ are each methyl.

In some embodiments, $R_3$, $R_7$, $R_{12}$, and $R_{18}$ are independently selected from the group consisting of aminoalkyloxy; aminoalkylcarboxy; alkylaminoalkyl; alkoxycarbonylalkyl; alkylcarbonylalkyl; di(alkyl)aminoalkyl; alkoxycarbonylalkyl; and alkylcarboxyalkyl.

In some embodiments, $R_3$, $R_7$, and $R_{12}$ are independently selected from the group consisting of aminoalkyloxy and aminoalkylcarboxy; and $R_{18}$ is selected from the group consisting of alkylaminoalkyl; alkoxycarbonylalkyl; alkylcarbonyloxyalkyl; di(alkyl)aminoalkyl; alkylaminoalkyl; alkyoxycarbonylalkyl; and alkylcarboxyalkyl.

In some embodiments, $R_3$, $R_7$, and $R_{12}$ are the same. In some embodiments, $R_3$, $R_7$, and $R_{12}$ are aminoalkyloxy. In some embodiments, $R_3$, $R_7$, and $R_{12}$ are aminoalkylcarboxy.

In some embodiments, R18 is alkylaminoalkyl. In some embodiments, alkoxycarbonylalkyl. In some embodiments, $R_{18}$ is di(alkyl)aminoalkyl. In some embodiments, $R_{18}$ is alkylcarboxyalkyl.

In some embodiments, $R_3$, $R_7$, $R_{12}$, and $R_{18}$ are independently selected from the group consisting of amino-$C_3$-alkyloxy; amino-$C_3$-alkyl-carboxy; $C_8$-alkylamino-$C_5$-alkyl; $C_8$-alkoxy-carbonyl-$C_4$-alkyl; $C_8$-alkyl-carbonyl-$C_4$-alkyl; di-($C_5$-alkyl)amino-$C_5$-alkyl; $C_{13}$-alkylamino-$C_5$-alkyl; $C_6$-alkoxy-carbonyl-$C_4$-alkyl; $C_6$-alkyl-carboxy-$C_4$-alkyl; and $C_{16}$-alkylamino-$C_5$-alkyl.

In some embodiments, m, n, and p are each 1 and q is 0.

In some embodiments, the CSA, or a pharmaceutically acceptable salt thereof, is:

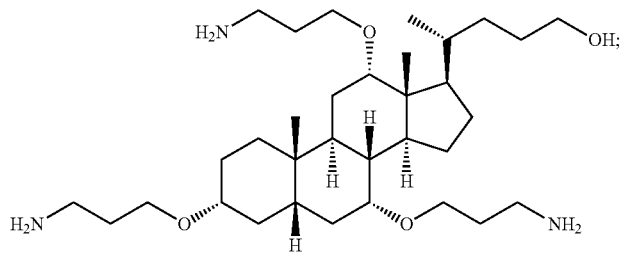

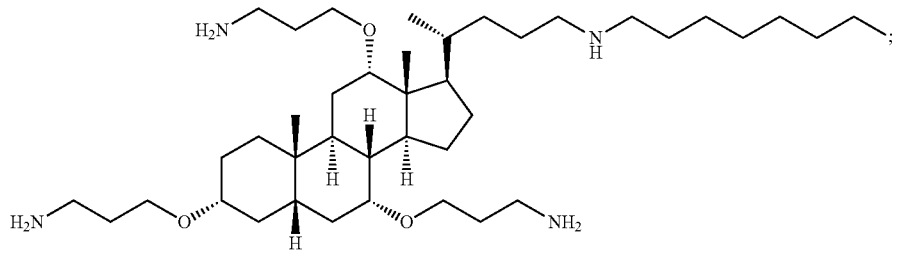

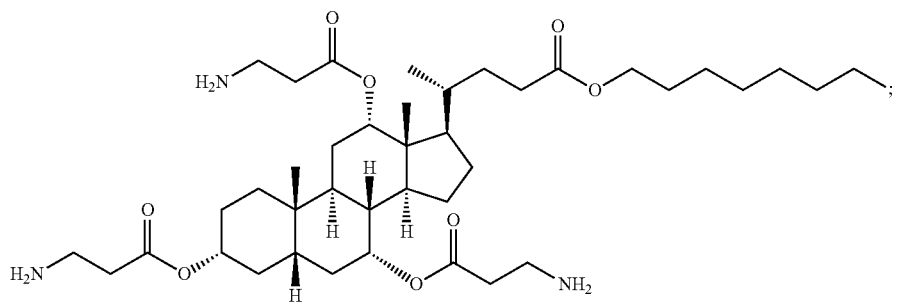

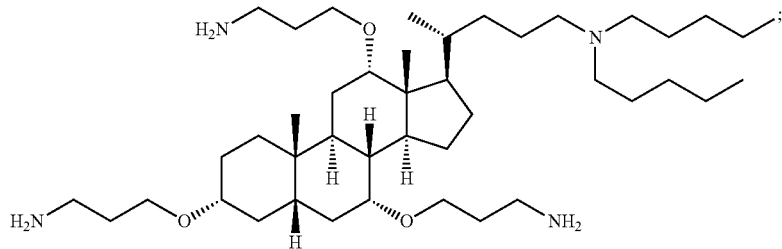

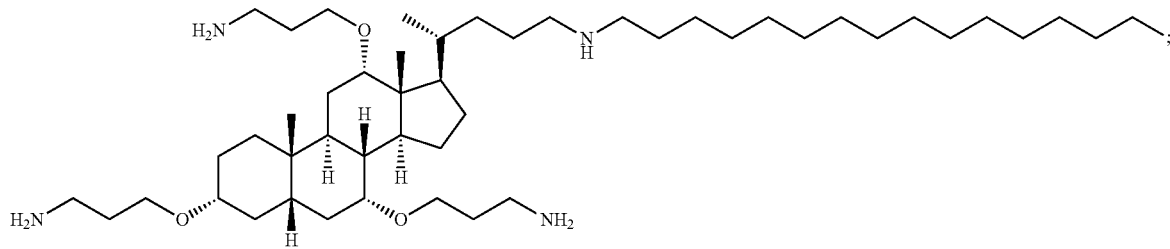

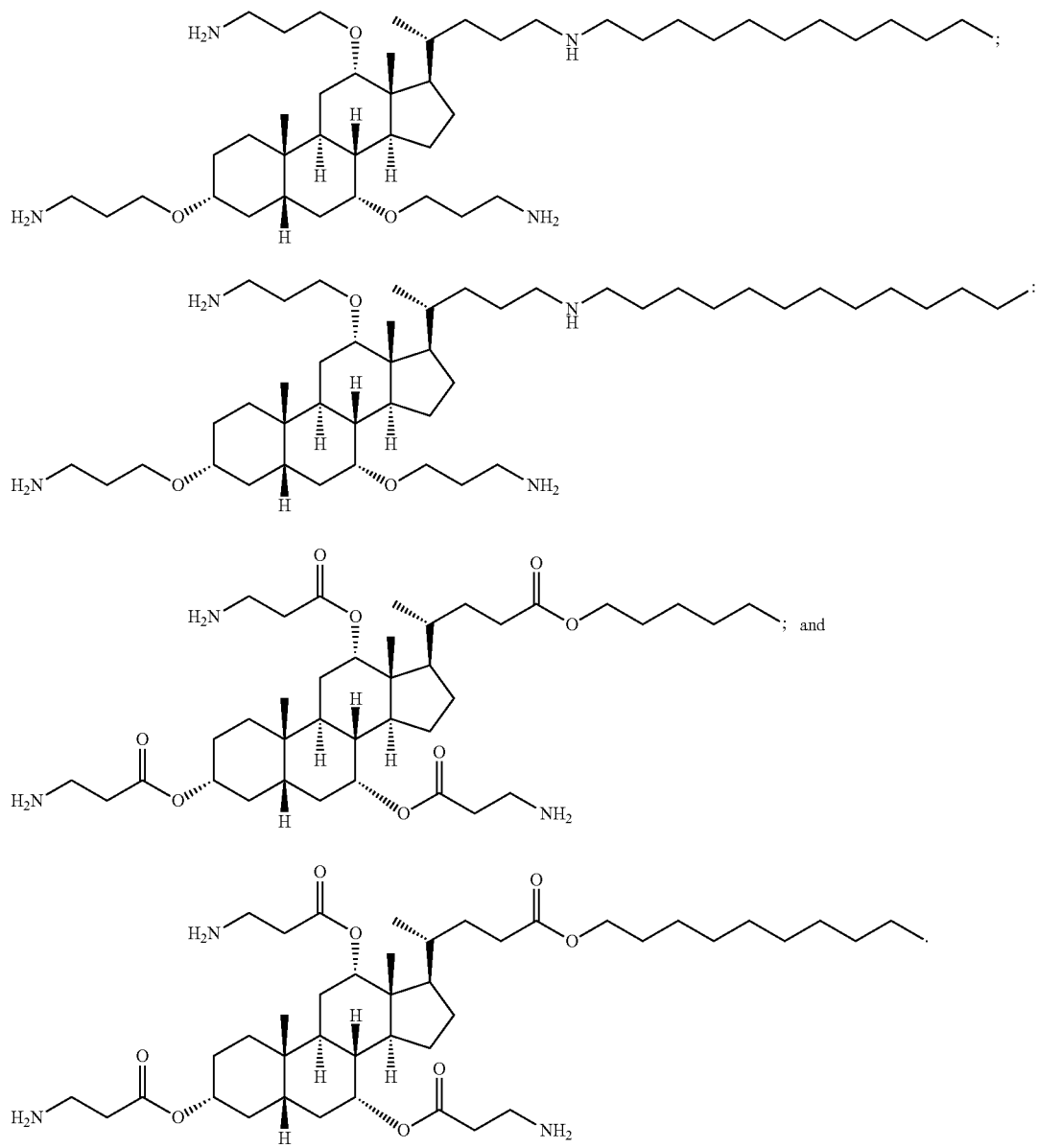
In some embodiments, the CSA, or a pharmaceutically acceptable salt thereof, is
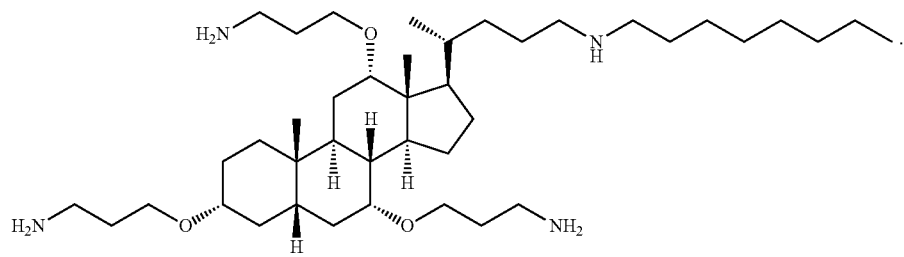
In other embodiments, the CSA, or a pharmaceutically acceptable salt thereof, is

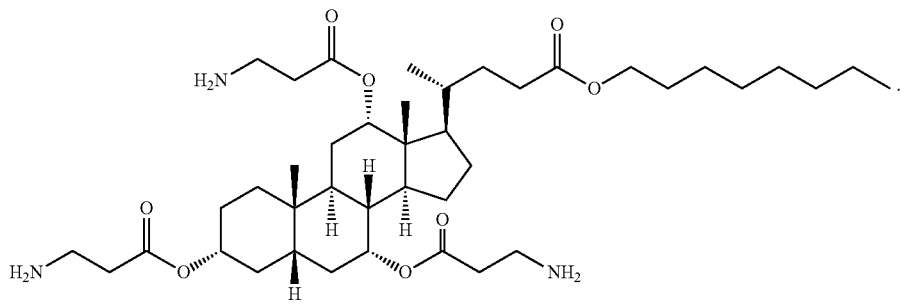

In other embodiments, the CSA, or a pharmaceutically acceptable salt thereof, is

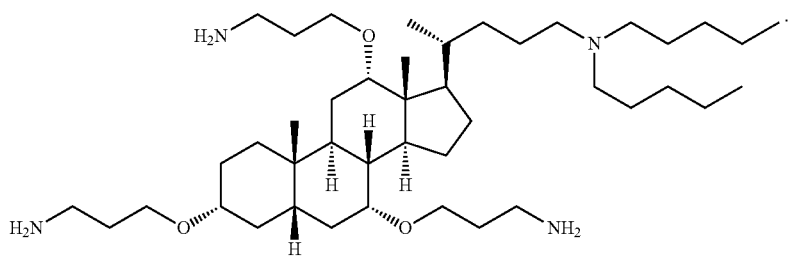

In other embodiments, the CSA, or a pharmaceutically acceptable salt thereof, is

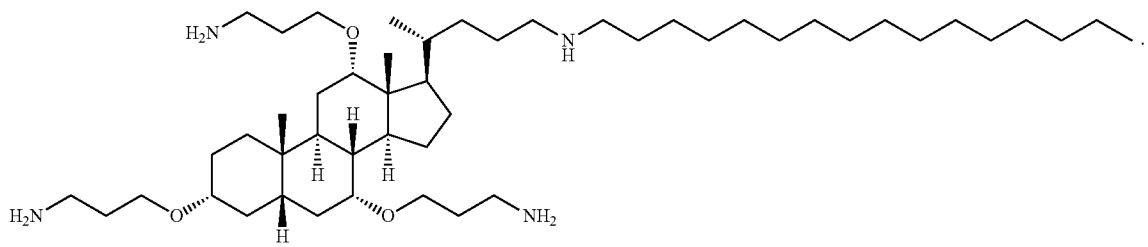

In some embodiments, the pharmaceutically acceptable salt is a hydrochloride salt. In some embodiments, the pharmaceutically acceptable salt is a mono-hydrochloride salt, a di-hydrochloride salt, a tri-hydrochloride salt, or a tetra-hydrochloride salt.

In some embodiments, the method further comprises administering a non-CSA chemotherapeutic agent to the patient. Such non-CSA chemotherapeutic agents include alkylating agents, anthracyclines, cytoskeletal disruptors, epothilones, histone deacetylase inhibitors, topoisomerase inhibitors, kinase inhibitors, monoclonal antibodies, nucleotide analogs, peptide antibiotics, platinum-based agents, retinoids, and vinca alkaloids.

In some embodiments, the method further comprises administering a compound to alleviate nausea and/or pain.

In some embodiments, the CSA is not

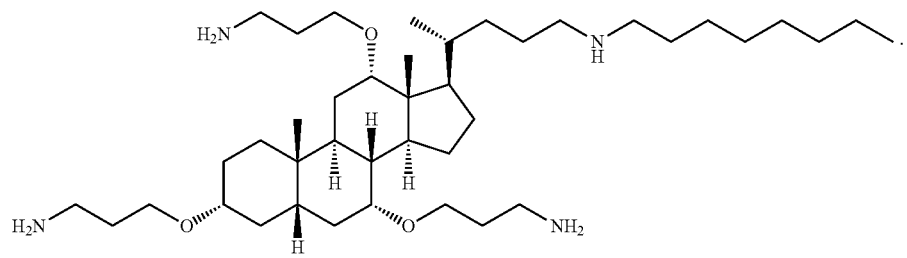

Some embodiments are directed to a compound having the following structure, or a pharmaceutically acceptable salt thereof:

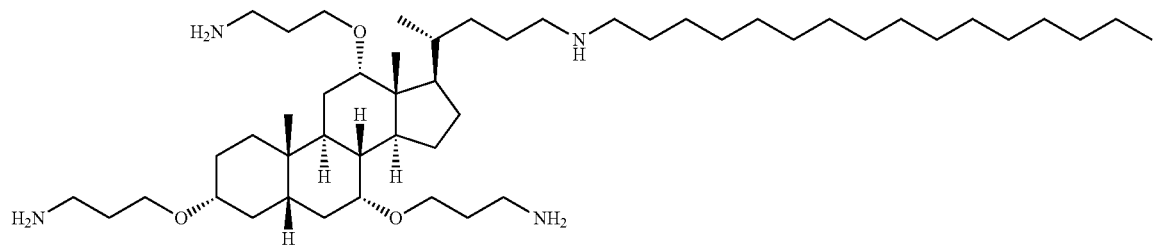

In some embodiments, the pharmaceutically acceptable salt is a hydrochloride salt, or specifically a tetra-hydrochloride salt.

Some embodiments are directed to the use of companion diagnostics to identify an appropriate treatment for the patient. In some embodiments, the CSA is selected by measuring a biomarker in the patient. The biomarker can be a cellular response to the CSA, such as cytotoxicity. In some embodiments, one or more chemotherapeutic agents are selected by subjecting a sample from the patient to a companion diagnostic device.

Some embodiments are directed to a CSA complexed with albumin and/or a surfactant. Other embodiments are directed to a pharmaceutical composition comprising CSA and albumin. Some embodiments are directed to a pharmaceutical composition comprising CSA and miranol.

Additional features and advantages will be set forth in part in the description that follows, and in part will be obvious from the description, or may be learned by practice of the embodiments disclosed herein. The objects and advantages of the embodiments disclosed herein will be realized and attained by means of the elements and combinations particularly pointed out in the appended claims. It is to be understood that both the foregoing brief summary and the following detailed description are exemplary and explanatory only and are not restrictive of the embodiments disclosed herein or as claimed.

DETAILED DESCRIPTION

The embodiments disclosed herein will now be described by reference to some more detailed embodiments, with occasional reference to the accompanying drawings. These embodiments may, however, be embodied in different forms and should not be construed as limited to the embodiments set forth herein. Rather, these embodiments are provided so that this disclosure will be thorough and complete, and will fully convey the scope of the embodiments to those skilled in the art.

Definitions:

Unless otherwise defined, all technical and scientific terms used herein have the same meaning as commonly understood by one of ordinary skill in the art to which these embodiments belong. The terminology used in the description herein is for describing particular embodiments only and is not intended to be limiting of the embodiments. As used in the specification and the appended claims, the singular forms "a," "an," and "the" are intended to include the plural forms as well, unless the context clearly indicates otherwise. All publications, patent applications, patents, and other references mentioned herein are incorporated by reference in their entirety.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof, and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present embodiments. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the embodiments are approximations, the numerical values set forth in the specific examples are reported as precisely as possible. Any numerical value, however, inherently contains certain errors necessarily resulting from the standard deviation found in their respective testing measurements. Every numerical range given throughout this specification and claims will include every narrower numerical range that falls within such broader numerical range, as if such narrower numerical ranges were all expressly written herein. Where a range of values is provided, it is understood that the upper and lower limit, and each intervening value between the upper and lower limit of the range is encompassed within the embodiments.

As used herein, any "R" group(s) such as, without limitation, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ represent substituents that can be attached to the indicated atom. Unless otherwise specified, an R group may be substituted or unsubstituted.

A "ring" as used herein can be heterocyclic or carbocyclic. The term "saturated" used herein refers to a ring having each atom in the ring either hydrogenated or substituted such that the valency of each atom is filled. The term "unsaturated" used herein refers to a ring where the valency of each atom of the ring may not be filled with hydrogen or other substituents. For example, adjacent carbon atoms in the fused ring can be doubly bound to each other. Unsaturation can also include deleting at least one of the following pairs and completing the valency of the ring carbon atoms at these deleted positions with a double bond; such as $R_5$ and $R_9$ $R_8$ and $R_{10}$; and $R_{13}$ and $R_{14}$.

Whenever a group is described as being "substituted" that group may be substituted with one, two, three or more of the indicated substituents, which may be the same or different, each replacing a hydrogen atom. If no substituents are indicated, it is meant that the indicated "substituted" group may be substituted with one or more group(s) individually and independently selected from alkyl, alkenyl, alkynyl, cycloalkyl, cycloalkenyl, cycloalkynyl, acylalkyl, alkoxyalkyl, aminoalkyl, amino acid, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen (e.g., F, Cl, Br, and I), thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, oxo, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, $R^aO(CH_2)_mO-$, $R^b(CH_2)_nO-$, $R^cC(O)O(CH_2)_pO-$, and protected derivatives thereof. The substituent may be attached to the group at more than one attachment point. For example, an aryl group may be substituted with a heteroaryl group at two attachment points to form a fused multicyclic aromatic ring system. Biphenyl and naphthalene are two examples of an aryl group that is substituted with a second aryl group.

As used herein, "$C_a$" or "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$ and $(CH_3)_3C-$. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 25 carbon atoms (whenever it appears herein, a numerical range such as "1 to 25" refers to each integer in the given range; e.g., "1 to 25 carbon atoms" means that the alkyl group may consist of 1 carbon atom, 2 carbon atoms, 3 carbon atoms, etc., up to and including 25 carbon atoms, although the present definition also covers the occurrence of the term "alkyl" where no numerical range is designated). The alkyl group may also be a medium size alkyl having 1 to 15 carbon atoms. The alkyl group could also be a lower alkyl having 1 to 6 carbon atoms. The alkyl group of the compounds may be designated as "$C_4$" or "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The alkenyl group may have 2 to 25 carbon atoms (whenever it appears herein, a numerical range such as "2 to 25" refers to each integer in the given range; e.g., "2 to 25 carbon atoms" means that the alkenyl group may consist of 2 carbon atom, 3 carbon atoms, 4 carbon atoms, etc., up to and including 25 carbon atoms, although the present definition also covers the occurrence of the term "alkenyl" where no numerical range is designated). The alkenyl group may also be a medium size alkenyl having 2 to 15 carbon atoms. The alkenyl group could also be a lower alkenyl having 1 to 6 carbon atoms. The alkenyl group of the compounds may be designated as "$C_4$" or "$C_2$-$C_4$ alkyl" or similar designations. An alkenyl group may be unsubstituted or substituted.

As used herein, "alkynyl" refers to an alkyl group that contains in the straight or branched hydrocarbon chain one or more triple bonds. The alkynyl group may have 2 to 25 carbon atoms (whenever it appears herein, a numerical range such as "2 to 25" refers to each integer in the given range; e.g., "2 to 25 carbon atoms" means that the alkynyl group may consist of 2 carbon atom, 3 carbon atoms, 4 carbon atoms, etc., up to and including 25 carbon atoms, although the present definition also covers the occurrence of the term "alkynyl" where no numerical range is designated). The alkynyl group may also be a medium size alkynyl having 2 to 15 carbon atoms. The alkynyl group could also be a lower alkynyl having 2 to 6 carbon atoms. The alkynyl group of the compounds may be designated as "$C_4$" or "$C_2$-$C_4$ alkyl" or similar designations. An alkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group (although the definition of $C_6$-$C_{10}$ aryl covers the occurrence of "aryl" when no numerical range is designated). Examples of aryl groups include, but are not limited to, benzene, naphthalene and azulene. An aryl group may be substituted or unsubstituted.

As used herein, "aralkyl" and "aryl(alkyl)" refer to an aryl group connected, as a substituent, via a lower alkylene group. The aralkyl group may have 6 to 20 carbon atoms (whenever it appears herein, a numerical range such as "6 to 20" refers to each integer in the given range; e.g., "6 to 20 carbon atoms" means that the aralkyl group may consist of 6 carbon atom, 7 carbon atoms, 8 carbon atoms, etc., up to and including 20 carbon atoms, although the present definition also covers the occurrence of the term "aralkyl" where no numerical range is designated). The lower alkylene and aryl group of an aralkyl may be substituted or unsubstituted. Examples include but are not limited to benzyl, 2-phenylalkyl, 3-phenylalkyl, and naphthylalkyl.

"Lower alkylene groups" refer to a $C_1$-$C_{25}$ straight-chained alkyl tethering groups, such as —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of"substituted."

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "alkoxy" or "alkyloxy" refers to the formula —OR wherein R is an alkyl, an alkenyl, an alkynyl, a cycloalkyl, a cycloalkenyl or a cycloalkynyl as defined above. A non-limiting list of alkoxys are methoxy, ethoxy, n-propoxy, 1-methylethoxy (isopropoxy), n-butoxy, iso-butoxy, sec-butoxy and tert-butoxy. An alkoxy may be substituted or unsubstituted.

As used herein, "acyl" refers to a hydrogen, alkyl, alkenyl, alkynyl, aryl, or heteroaryl connected, as substituents, via a carbonyl group. Examples include formyl, acetyl, propanoyl, benzoyl, and acryl. An acyl may be substituted or unsubstituted.

As used herein, "alkoxyalkyl" or "alkyloxyalkyl" refers to an alkoxy group connected, as a substituent, via a lower alkylene group. Examples include alkyl-O-alkyl- and alkoxy-alkyl- with the terms alkyl and alkoxy defined herein.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

The term "amino" as used herein refers to a —NH$_2$ group.

As used herein, the term "hydroxy" refers to a —OH group.

A "cyano" group refers to a "—CN" group.

A "carbonyl" or an "oxo" group refers to a C=O group.

The term "azido" as used herein refers to a —N$_3$ group.

As used herein, "aminoalkyl" refers to an amino group connected, as a substituent, via a lower alkylene group. Examples include H$_2$N-alkyl- with the term alkyl defined herein.

As used herein, "alkylcarboxyalkyl" refers to an alkyl group connected, as a substituent, to a carboxy group that is connected, as a substituent, to an alkyl group. Examples include alkyl-C(=O)O-alkyl- and alkyl-O—C(=O)-alkyl- with the term alkyl as defined herein.

As used herein, "alkylaminoalkyl" refers to an alkyl group connected, as a substituent, to an amino group that is connected, as a substituent, to an alkyl group. Examples include alkyl-NH-alkyl-, with the term alkyl as defined herein.

As used herein, "dialkylaminoalkyl" or "di(alkyl)aminoalkyl" refers to two alkyl groups connected, each as a substituent, to an amino group that is connected, as a substituent, to an alkyl group. Examples include

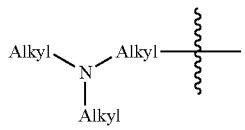

with the term alkyl as defined herein.

As used herein, "alkylaminoalkylamino" refers to an alkyl group connected, as a substituent, to an amino group that is connected, as a substituent, to an alkyl group that is connected, as a substituent, to an amino group. Examples include alkyl-NH-alkyl-NH—, with the term alkyl as defined herein.

As used herein, "alkylaminoalkylaminoalkylamino" refers to an alkyl group connected, as a substituent, to an amino group that is connected, as a substituent, to an alkyl group that is connected, as a substituent, to an amino group that is connected, as a substituent, to an alkyl group. Examples include alkyl-NH-alkyl-NH-alkyl-, with the term alkyl as defined herein.

As used herein, "arylaminoalkyl" refers to an aryl group connected, as a substituent, to an amino group that is connected, as a substituent, to an alkyl group. Examples include aryl-NH-alkyl-, with the terms aryl and alkyl as defined herein.

As used herein, "aminoalkyloxy" refers to an amino group connected, as a substituent, to an alkyloxy group. Examples include H$_2$N-alkyl-O— and H$_2$N-alkoxy- with the terms alkyl and alkoxy as defined herein.

As used herein, "aminoalkyloxyalkyl" refers to an amino group connected, as a substituent, to an alkyloxy group connected, as a substituent, to an alkyl group. Examples include H2N-alkyl-O-alkyl- and H$_2$N-alkoxy-alkyl- with the terms alkyl and alkoxy as defined herein.

As used herein, "aminoalkylcarboxy" refers to an amino group connected, as a substituent, to an alkyl group connected, as a substituent, to a carboxy group. Examples include H$_2$N-alkyl-C(=O)O— and H$_2$N-alkyl-O—C(=O)— with the term alkyl as defined herein.

As used herein, "aminoalkylaminocarbonyl" refers to an amino group connected, as a substituent, to an alkyl group connected, as a substituent, to an amino group connected, as a substituent, to a carbonyl group. Examples include H$_2$N-alkyl-NH—C(=O)— with the term alkyl as defined herein.

As used herein, "aminoalkylcarboxamido" refers to an amino group connected, as a substituent, to an alkyl group connected, as a substituent, to a carbonyl group connected, as a substituent to an amino group. Examples include H$_2$N-alkyl-C(=O)—NH— with the term alkyl as defined herein.

As used herein, "azidoalkyloxy" refers to an azido group connected as a substituent, to an alkyloxy group. Examples include N$_3$-alkyl-O— and N$_3$-alkoxy- with the terms alkyl and alkoxy as defined herein.

As used herein, "cyanoalkyloxy" refers to a cyano group connected as a substituent, to an alkyloxy group. Examples include NC-alkyl-O— and NC-alkoxy- with the terms alkyl and alkoxy as defined herein.

As used herein, "guanidinoalkyloxy" refers to a guanidinyl group connected, as a substituent, to an alkyloxy group. Examples include

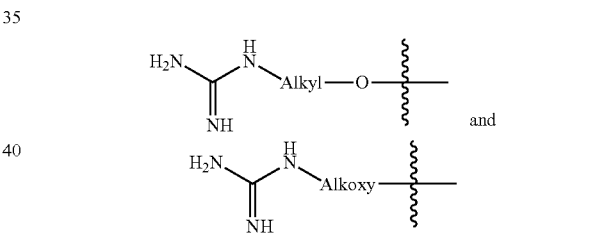

with the terms alkyl and alkoxy as defined herein.

As used herein, "guanidinoalkylcarboxy" refers to a guanidinyl group connected, as a substituent, to an alkyl group connected, as a substituent, to a carboxy group. Examples include

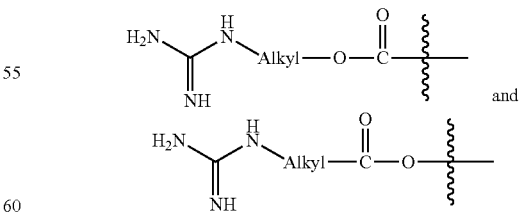

with the term alkyl as defined herein.

As used herein, "quaternary ammonium alkylcarboxy" refers to a quaternized amino group connected, as a substituent, to an alkyl group connected, as a substituent, to a carboxy group. Examples include

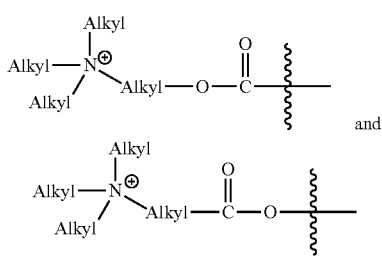

and with the term alkyl as defined herein.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens.

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine.

A linking group is a divalent moiety used to link one steroid to another steroid. In some embodiments, the linking group is used to link a first CSA with a second CSA (which may be the same or different). An example of a linking group is $(C_1-C_{10})$ alkyloxy-$(C_1-C_{10})$ alkyl.

The terms "P.G." or "protecting group" or "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propyl silyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4"-trimethoxytrityl (TMTr); and those described herein). Amino-protecting groups are known to those skilled in the art. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that compound is within the disclosure.

Compounds:

Compounds useful in accordance with this disclosure are described herein, both generically and with particularity, and in U.S. Pat. Nos. 6,350,738, 6,486,148, 6,767,904, 7,598,234, and 7,754,705, which are incorporated herein by reference. Compounds include steroid derivatives, such as cationic steroid antimicrobials ("CSAs") that exhibit one or more anti-cancer and/or anti-proliferative activities or functions. The skilled artisan will recognize the compounds within the generic formula set forth herein. Additional compounds of the disclosure having one or more anti-cancer and/or anti-proliferative activities or functions are described and can be characterized using the assays set forth herein and in the art. Methods and Uses:

Disclosed herein are methods of treating cancer comprising identifying a patient in need of treatment and administering a therapeutically effective amount of at least one cationic steroid antimicrobial (CSA), or a pharmaceutically acceptable salt thereof. Disclosed herein are also methods of reducing cellular proliferation comprising contacting a cationic steroid antimicrobial (CSA) with a cell selected from the group consisting of: CCRF-CEM; HL-60(TB); K-562; MOLT-4; RPMI-8226; SR; A549/ATCC; EKVX; HOP-62; HOP-92; NCI-H226; NCI-H23; NCI-H322M; NCI-H460; NCI-H522; COLO 205; HCC-2998; HCT-116; HCT-15; HT29; KM12; SW-620; SF-268; SF-295; SF-539; SNB-19; SNB-75; U251; LOX IMVI; MALME-3M; M14; SK-MEL-2; SK-MEL-28; SK-MEL-5; UACC-257; UACC-62; IGROV1; OVCAR-3; OVCAR-4; OVCAR-5; OVCAR-8; NCI/ADR-RES; SK-OV-3; 786-0; A4981; ACHN; CAKI-1; RXF 393; SN12C; TK-10; UO-31; PC-3; DU-145; MCF7; NCI-ADR-RES; MDA-MB-231/ATCC; HS 578T; MDA-MB-435; MDA-MB-468; BT-549; and T-47D. Also contemplated is treating a cancer patient having cancer of a type represented by or characterized by one of the foregoing cell lines, by administering an effective anti-cancer amount of a CSA to the patient.

In some embodiments, the cancer is leukemia, non-small cell lung cancer, colon cancer, CNS cancer, skin cancer, ovarian cancer, renal cancer, prostate cancer, breast cancer, or multiple myeloma. In other embodiments, the skin cancer is melanoma.

Some embodiments disclosed herein relate to a method of treating cancer and/or reducing cellular proliferation by administering a compound of Formula (I) or a pharmaceutically acceptable salt thereof:

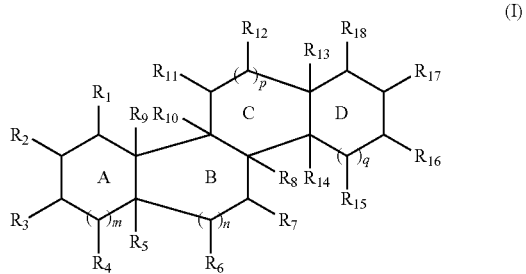

(I)

wherein rings A, B, C, and D are independently saturated, or are fully or partially unsaturated, provided that at least two of rings A, B, C, and D are saturated; m, n, p, and q are independently 0 or 1; $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted alkyl, substituted or unsubstituted hydroxyalkyl, substituted or unsubstituted alkyloxyalkyl, substituted or unsubstituted alkylcarboxyalkyl, substituted or unsubstituted alkylaminoalkyl, substituted or unsubstituted alkylaminoalkylamino, substituted or unsubstituted alkylaminoalkylaminoalkylamino, a substituted or unsubstituted aminoalkyl, a substituted or unsubstituted aryl, a substituted or unsubstituted arylaminoalkyl, substituted or unsubstituted haloalkyl, substituted or unsubstituted alkenyl, substituted or unsubstituted alkynyl, oxo, a linking group attached to a second steroid, a substituted or unsubstituted aminoalkyloxy, a substituted or unsubstituted aminoalkyloxyalkyl, a substituted or unsubstituted aminoalkylcarboxy, a substituted or unsubstituted aminoalkylaminocarbonyl, a substituted or unsubstituted aminoalkylcarboxamido, a substituted or unsubstituted di(alkyl)aminoalkyl, $H_2N-HC(Q_5)-C(O)-O-$, $H_2N-HC(Q_5)-C(O)-N(H)-$, substituted or unsubstituted azidoalkyloxy, substituted or unsubstituted cyanoalkyloxy, P.G.-HN-HC($Q_5$)-C(O)-O-, substituted or unsubstituted guanidinoalkyloxy, substituted or unsubstituted quaternary ammonium alkylcarboxy, and substituted or unsubstituted guanidinoalkyl carboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted alkyl, substituted or unsubstituted hydroxyalkyl, substituted or unsubstituted alkyloxyalkyl, a substituted or unsubstituted aminoalkyl, a substituted or unsubstituted aryl, substituted or unsubstituted haloalkyl, substituted or unsubstituted alkenyl, substituted or unsubstituted alkynyl, oxo, a linking group attached to a second steroid, a substituted or unsubstituted aminoalkyloxy, a substituted or unsubstituted aminoalkylcarboxy, a substituted or unsubstituted aminoalkylaminocarbonyl, a substituted or unsubstituted di(alkyl)aminoalkyl, $H_2N-HC(Q_5)-C(O)-O-$, $H_2N-HC(Q_5)-C(O)-N(H)-$, substituted or unsubstituted azidoalkyloxy, substituted or unsubstituted cyanoalkyloxy, P.G.-HN-HC($Q_5$)-C(O)-O-, substituted or unsubstituted guanidinoalkyloxy, and substituted or unsubstituted guanidinoalkyl carboxy, where $Q_5$ is a side chain of any amino acid, P.G. is an amino protecting group; provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted aminoalkyl, a substituted or unsubstituted aminoalkyloxy, substituted or unsubstituted alkylcarboxyalkyl, substituted or unsubstituted alkylaminoalkylamino, substituted or unsubstituted alkylaminoalkylaminoalkylamino, a substituted or unsubstituted aminoalkylcarboxy, a substituted or unsubstituted arylaminoalkyl, a substituted or unsubstituted aminoalkyloxyaminoalkylaminocarbonyl, a substituted or unsubstituted aminoalkylaminocarbonyl, a substituted or unsubstituted aminoalkylcarboxyamido, a substituted or unsubstituted quaternary ammonium alkylcarboxy, a substituted or unsubstituted di(alkyl)aminoalkyl, $H_2N-HC(Q_5)-C(O)-O-$, $H_2N-HC(Q_5)-C(O)-N(H)-$, substituted or unsubstituted azidoalkyloxy, substituted or unsubstituted cyanoalkyloxy, P.G.-HN-HC(Q5)-C(O)-O-, substituted or unsubstituted guanidinoalkyloxy, and a substituted or unsubstituted guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted ($C_1$-$C_{18}$) alkyl, substituted or unsubstituted ($C_1$-$C_{18}$) hydroxyalkyl, substituted or unsubstituted ($C_1$-$C_{18}$) alkyloxy-($C_1$-$C_{18}$) alkyl, substituted or unsubstituted ($C_1$-$C_{18}$) alkylcarboxy-($C_1$-$C_{18}$) alkyl, substituted or unsubstituted ($C_1$-$C_{18}$) alkylamino-($C_1$-$C_{18}$)alkyl, substituted or unsubstituted ($C_1$-$C_{18}$) alkylamino-($C_1$-$C_{18}$) alkylamino, substituted or unsubstituted ($C_1$-$C_{18}$) alkylamino-($C_1$-$C_{18}$) alkylamino-($C_1$-$C_{18}$) alkylamino, a substituted or unsubstituted ($C_1$-$C_{18}$) aminoalkyl, a substituted or unsubstituted aryl, a substituted or unsubstituted arylamino-($C_1$-$C_{18}$) alkyl, substituted or unsubstituted ($C_1$-$C_{18}$) haloalkyl, substituted or unsubstituted ($C_2$-$C_6$) alkenyl, substituted or unsubstituted ($C_2$-$C_6$) alkynyl, oxo, a linking group attached to a second steroid, a substituted or unsubstituted ($C_1$-$C_{18}$) aminoalkyloxy, a substituted or unsubstituted ($C_1$-$C_{18}$) aminoalkyloxy-($C_1$-$C_{18}$) alkyl, substituted or unsubstituted ($C_1$-$C_{18}$) aminoalkylcarboxy, a substituted or unsubstituted ($C_1$-$C_{18}$) aminoalkylaminocarbonyl, a substituted or unsubstituted ($C_1$-$C_{18}$) aminoalkylcarboxamido, a substituted or unsubstituted di($C_1$-$C_{18}$ alkyl)aminoalkyl, $H_2N-HC(Q_5)-C(O)-O-$, $H_2N-HC(Q_5)-C(O)-N(H)-$, substituted or unsubstituted ($C_1$-$C_{18}$) azidoalkyloxy, substituted or unsubstituted ($C_1$-$C_{18}$) cyanoalkyloxy, P.G.-HN-HC($Q_5$)-C(O)-O-, substituted or unsubstituted ($C_1$-$C_{18}$) guanidinoalkyloxy, substituted or unsubstituted ($C_1$-$C_{18}$) quaternary ammonium alkylcarboxy, and substituted or unsubstituted ($C_1$-$C_{18}$) guanidinoalkyl carboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted ($C_1$-$C_{18}$) alkyl, substituted or unsubstituted ($C_1$-$C_{18}$) hydroxyalkyl, substituted or unsubstituted ($C_1$-$C_{18}$) alkyloxy-($C_1$-$C_{18}$) alkyl, a substituted or unsubstituted ($C_1$-$C_{18}$) aminoalkyl, a substituted or unsubstituted aryl, substituted or unsubstituted ($C_1$-$C_{18}$) haloalkyl, substituted or unsubstituted ($C_2$-$C_6$) alkenyl, substituted or unsubstituted ($C_2$-$C_6$) alkynyl, oxo, a linking group attached to a second steroid, a substituted or unsubstituted ($C_1$-$C_{18}$) aminoalkyloxy, a substituted or unsubstituted ($C_1$-$C_{18}$) aminoalkylcarboxy, a substituted or unsubstituted ($C_1$-$C_{18}$) aminoalkylaminocarbonyl, di($C_1$-$C_{18}$ alkyl)aminoalkyl, $H_2N-HC(Q_5)-C(O)-O-$, $H_2N-HC(Q_5)-C(O)-N(H)-$, substituted or unsubstituted ($C_1$-$C_{18}$) azidoalkyloxy, substituted or unsubstituted ($C_1$-$C_{18}$)

cyanoalkyloxy, P.G.-HN—HC(Q$_5$)-C(O)—O—, substituted or unsubstituted (C$_1$-C$_{18}$) guanidinoalkyloxy, and substituted or unsubstituted (C$_1$-C$_{18}$) guanidinoalkylcarboxy, where Q5 is a side chain of any amino acid, and P.G. is an amino protecting group; provided that at least two or three of R$_{1-4}$, R$_6$, R$_7$, R$_{11}$, R$_{12}$, R$_{15}$, R$_{16}$, R$_{17}$, and R$_{18}$ are independently selected from the group consisting of a substituted or unsubstituted (C$_1$-C$_{18}$) aminoalkyl, a substituted or unsubstituted (C$_1$-C$_{18}$) aminoalkyloxy, substituted or unsubstituted (C$_1$-C$_{18}$) alkylcarboxy-(C$_1$-C$_{18}$) alkyl, substituted or unsubstituted (C$_1$-C$_{18}$) alkylamino-(C$_1$-C$_{18}$) alkylamino, substituted or unsubstituted (C$_1$-C$_{18}$) alkylamino-(C$_1$-C$_{18}$) alkylamino (C$_1$-C$_{18}$) alkylamino, a substituted or unsubstituted (C$_1$-C$_{18}$) aminoalkylcarboxy, a substituted or unsubstituted arylamino (C$_1$-C$_{18}$) alkyl, a substituted or unsubstituted (C$_1$-C$_{18}$) aminoalkyloxy (C$_1$-C$_{18}$) aminoalkylaminocarbonyl, a substituted or unsubstituted (C$_1$-C$_{18}$) aminoalkylaminocarbonyl, a substituted or unsubstituted (C$_1$-C$_{18}$) aminoalkylcarboxyamido, a substituted or unsubstituted (C$_1$-C$_{18}$) quaternary ammonium alkylcarboxy, substituted or unsubstituted di(C$_1$-C$_{18}$ alkyl)aminoalkyl, H$_2$N—HC(Q$_5$)-C(O)—O—, H$_2$N—HC(Q$_5$)-C(O)—N(H)—, substituted or unsubstituted (C$_1$-C$_{18}$) azidoalkyloxy, substituted or unsubstituted (C$_1$-C$_{18}$) cyanoalkyloxy, P.G.-HN—HC(Q5)-C(O)—O—, substituted or unsubstituted (C$_1$-C$_{18}$) guanidinoalkyloxy, and a substituted or unsubstituted (C$_1$-C$_{18}$) guanidinoalkylcarboxy.

In some embodiments, R$_1$ through R$_4$, R$_6$, R$_7$, R$_{11}$, R$_{12}$, R$_{15}$, R$_{16}$, and R$_{18}$ are independently selected from the group consisting of hydrogen, hydroxyl, an unsubstituted (C$_1$-C$_{18}$) alkyl, unsubstituted (C$_1$-C$_{18}$) hydroxyalkyl, unsubstituted (C$_1$-C$_{18}$) alkyloxy-(C$_1$-C$_{18}$)alkyl, unsubstituted (C$_1$-C$_{18}$) alkylcarboxy-(C$_1$-C$_{18}$) alkyl, unsubstituted (C$_1$-C$_{18}$) alkylamino-(C$_1$-C$_{18}$)alkyl, unsubstituted (C$_1$-C$_{18}$) alkylamino-(C$_1$-C$_{18}$) alkylamino, unsubstituted (C$_1$-C$_{18}$) alkylamino-(C$_1$-C$_{18}$) alkylamino-(C$_1$-C$_{18}$) alkylamino, an unsubstituted (C$_1$-C$_{18}$) aminoalkyl, an unsubstituted aryl, an unsubstituted arylamino-(C$_1$-C$_{18}$) alkyl, oxo, an unsubstituted (C$_1$-C$_{18}$) aminoalkyloxy, an unsubstituted (C$_1$-C$_{18}$) aminoalkyloxy-(C$_1$-C$_{18}$) alkyl, an unsubstituted (C$_1$-C$_{18}$) aminoalkylcarboxy, an unsubstituted (C$_1$-C$_{18}$) aminoalkylaminocarbonyl, an unsubstituted (C$_1$-C$_{18}$) aminoalkylcarboxamido, an unsubstituted di(C$_1$-C$_{18}$ alkyl)aminoalkyl, unsubstituted (C$_1$-C$_{18}$) guanidinoalkyloxy, unsubstituted (C$_1$-C$_{18}$) quaternary ammonium alkylcarboxy, and unsubstituted (C$_1$-C$_{18}$) guanidinoalkyl carboxy; and R$_5$, R$_8$, R$_9$, R$_{10}$, R$_{13}$, R$_{14}$ and R$_{17}$ are independently deleted when one of rings A, B, C, or D is unsaturated so as to complete the valency of the carbon atom at that site, or R$_5$, R$_8$, R$_9$, R$_{10}$, R$_{13}$, and R$_{14}$ are independently selected from the group consisting of hydrogen, hydroxyl, an unsubstituted (C$_1$-C$_{18}$) alkyl, unsubstituted (C$_1$-C$_{18}$) hydroxyalkyl, unsubstituted (C$_1$-C$_{18}$) alkyloxy-(C$_1$-C$_{18}$) alkyl, unsubstituted (C$_1$-C$_{18}$) alkylcarboxy-(C$_1$-C$_{18}$) alkyl, unsubstituted (C$_1$-C$_{18}$) alkylamino-(C$_1$-C$_{18}$) alkyl, unsubstituted (C$_1$-C$_{18}$) alkylamino-(C$_1$-C$_{18}$) alkylamino, unsubstituted (C$_1$-C$_{18}$) alkylamino-(C$_1$-C$_{18}$) alkylamino-(C$_1$-C$_{18}$) alkylamino, an unsubstituted (C$_1$-C$_{18}$) aminoalkyl, an unsubstituted aryl, an unsubstituted arylamino-(C$_1$-C$_{18}$) alkyl, oxo, an unsubstituted (C$_1$-C$_{18}$) aminoalkyloxy, an unsubstituted (C$_1$-C$_{18}$) aminoalkyloxy-(C$_1$-C$_{18}$) alkyl, an unsubstituted (C$_1$-C$_{18}$) aminoalkylcarboxy, an unsubstituted (C$_1$-C$_{18}$) aminoalkylaminocarbonyl, an unsubstituted (C$_1$-C$_{18}$) aminoalkylcarboxamido, an unsubstituted di(C$_1$-C$_{18}$ alkyl)aminoalkyl, unsubstituted (C$_1$-C$_{18}$) guanidinoalkyloxy, unsubstituted (C$_1$-C$_{18}$) quaternary ammonium alkylcarboxy, and unsubstituted (C$_1$-C$_{18}$) guanidinoalkyl carboxy; provided that at least two or three of R$_{1-4}$, R$_6$, R$_7$, R$_{11}$, R$_{12}$, R$_{15}$, R$_{16}$, R$_{17}$, and R$_{18}$ are independently selected from the group consisting of hydrogen, hydroxyl, an unsubstituted (C$_1$-C$_{18}$) alkyl, unsubstituted (C$_1$-C$_{18}$) hydroxyalkyl, unsubstituted (C$_1$-C$_{18}$) alkyloxy-(C$_1$-C$_{18}$) alkyl, unsubstituted (C$_1$-C$_{18}$) alkylcarboxy-(C$_1$-C$_{18}$) alkyl, unsubstituted (C$_1$-C$_{18}$) alkylamino-(C$_1$-C$_{18}$) alkyl, unsubstituted (C$_1$-C$_{18}$) alkylamino-(C$_1$-C$_{18}$) alkylamino, unsubstituted (C$_1$-C$_{18}$) alkylamino-(C$_1$-C$_{18}$) alkylamino-(C$_1$-C$_{18}$) alkylamino, an unsubstituted (C$_1$-C$_{18}$) aminoalkyl, an unsubstituted aryl, an unsubstituted arylamino-(C$_1$-C$_{18}$) alkyl, oxo, an unsubstituted (C$_1$-C$_{18}$) aminoalkyloxy, an unsubstituted (C$_1$-C$_{18}$) aminoalkyloxy-(C$_1$-C$_{18}$) alkyl, an unsubstituted (C$_1$-C$_{18}$) aminoalkylcarboxy, an unsubstituted (C$_1$-C$_{18}$) aminoalkylaminocarbonyl, an unsubstituted (C$_1$-C$_{18}$) aminoalkylcarboxamido, an unsubstituted di(C$_1$-C$_{18}$ alkyl)aminoalkyl, unsubstituted (C$_1$-C$_{18}$) guanidinoalkyloxy, unsubstituted (C$_1$-C$_{18}$) quaternary ammonium alkylcarboxy, and unsubstituted (C$_1$-C$_{18}$) guanidinoalkyl carboxy.

In some embodiments, the CSA, or pharmaceutically acceptable salts thereof of Formula (I), can be also represented by Formula (II):

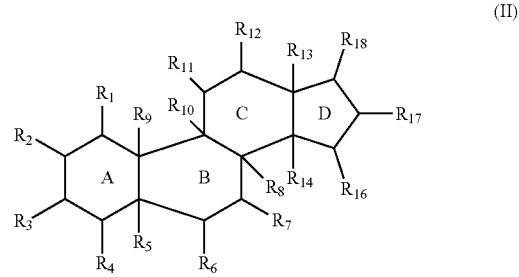

In some embodiments, rings A, B, C, and D are independently saturated.

In some embodiments, one or more of rings A, B, C, and D are heterocyclic.

In some embodiments, rings A, B, C, and D are non-heterocyclic.

In some embodiments, R$_3$, R$_7$, R$_{12}$, and R$_{18}$ are independently selected from the group consisting of hydrogen, an unsubstituted (C$_1$-C$_{18}$) alkyl, unsubstituted (C$_1$-C$_{18}$) hydroxyalkyl, unsubstituted (C$_1$-C$_{18}$) alkyloxy-(C$_1$-C$_{18}$) alkyl, unsubstituted (C$_1$-C$_{18}$) alkylcarboxy-(C$_1$-C$_{18}$) alkyl, unsubstituted (C$_1$-C$_{18}$) alkylamino-(C$_1$-C$_{18}$)alkyl, unsubstituted (C$_1$-C$_{18}$) alkylamino-(C$_1$-C$_{18}$) alkylamino, unsubstituted (C$_1$-C$_{18}$) alkylamino-(C$_1$-C$_{18}$) alkylamino-(C$_1$-C$_{18}$) alkylamino, an unsubstituted (C$_1$-C$_{18}$) aminoalkyl, an unsubstituted arylamino-(C$_1$-C$_{18}$) alkyl, an unsubstituted (C$_1$-C$_{18}$) aminoalkyloxy, an unsubstituted (C$_1$-C$_{18}$) aminoalkyloxy-(C$_1$-C$_{18}$) alkyl, an unsubstituted (C$_1$-C$_{18}$) aminoalkylcarboxy, an unsubstituted (C$_1$-C$_{18}$) aminoalkylaminocarbonyl, an unsubstituted (C$_1$-C$_{18}$) aminoalkylcarboxamido, an unsubstituted di(C$_1$-C$_{18}$ alkyl)aminoalkyl, unsubstituted (C$_1$-C$_{18}$) guanidinoalkyloxy, unsubstituted (C$_1$-C$_{18}$) quaternary ammonium alkylcarboxy, and unsubstituted (C$_1$-C$_{18}$) guanidinoalkyl carboxy; and R$_1$, R$_2$, R$_4$, R$_5$, R$_6$, R$_8$, R$_9$, R$_{10}$, R$_{11}$, R$_{13}$, R$_{14}$, R$_{15}$, R$_{16}$, and R$_{17}$ are independently selected from the group consisting of hydrogen and unsubstituted (C$_1$-C$_6$) alkyl.

In some embodiments, R$_3$, R$_7$, R$_{12}$, R$_{18}$ are independently selected from the group consisting of hydrogen, an unsubstituted (C$_1$-C$_6$) alkyl, unsubstituted (C$_1$-C$_6$) hydroxyalkyl, unsubstituted (C$_1$-C$_{16}$) alkyloxy-(C$_1$-C$_5$) alkyl, unsubstituted (C$_1$-C$_{16}$) alkylcarboxy-(C$_1$-C$_5$) alkyl, unsubstituted (C$_1$-C$_{16}$) alkylamino-(C$_1$-C$_5$)alkyl, unsubstituted (C$_1$-C$_{16}$) alkylamino-(C$_1$-C$_5$) alkylamino, unsubstituted (C$_1$-C$_{16}$) alkylamino-(C$_1$-C$_{16}$) alkylamino-(C$_1$-C$_5$) alkylamino, an unsubstituted (C$_1$-C$_{16}$) aminoalkyl, an unsubstituted arylamino-(C$_1$-C$_5$) alkyl, an unsubstituted (C$_1$-C$_5$) aminoalkyloxy, an unsubstituted (C$_1$-C$_{16}$) aminoalkyloxy-(C$_1$-C$_5$) alkyl, an unsubstituted (C$_1$-C$_5$) aminoalkylcarboxy, an unsubstituted (C$_1$-C$_5$) aminoalkylaminocarbonyl, an unsubstituted (C$_1$-C$_5$) aminoalkylcarboxamido, an unsubstituted di(C$_1$-C$_5$ alkyl)amino-(C$_1$-C$_5$) alkyl, unsubstituted (C$_1$-C$_5$) guanidinoalkyloxy, unsubstituted (C$_1$-C$_{16}$) quaternary ammonium alkylcarboxy, and unsubstituted (C$_1$-C$_{16}$) guanidinoalkylcarboxy;

In some embodiments, $R_1$, $R_2$, $R_4$, $R_5$, $R_6$, $R_8$, $R_{10}$, $R_{11}$, $R_{14}$, $R_{16}$, and $R_{17}$ are each hydrogen; and $R_9$ and $R_{13}$ are each methyl.

In some embodiments, $R_3$, $R_7$, $R_{12}$, and $R_{18}$ are independently selected from the group consisting of aminoalkyloxy; aminoalkylcarboxy; alkylaminoalkyl; alkoxycarbonylalkyl; alkylcarbonylalkyl; di(alkyl)aminoalkyl; alkoxycarbonylalkyl; and alkylcarboxyalkyl.

In some embodiments, $R_3$, $R_7$, and $R_{12}$ are independently selected from the group consisting of aminoalkyloxy and aminoalkylcarboxy; and $R_{18}$ is selected from the group consisting of alkylaminoalkyl; alkoxycarbonylalkyl; alkylcarbonyloxyalkyl; di(alkyl)aminoalkyl; alkylaminoalkyl; alkyoxycarbonylalkyl; and alkylcarboxyalkyl.

In some embodiments, $R_3$, $R_7$, and $R_{12}$ are the same.

In some embodiments, $R_3$, $R_7$, and $R_{12}$ are aminoalkyloxy.

In some embodiments, $R_3$, $R_7$, and $R_{12}$ are aminoalkylcarboxy.

In some embodiments, $R_{18}$ is alkylaminoalkyl.
In some embodiments, $R_{18}$ is alkoxycarbonylalkyl.
In some embodiments, $R_{18}$ is di(alkyl)aminoalkyl.
In some embodiments, $R_{18}$ is alkylcarboxyalkyl.

In some embodiments, $R_3$, $R_7$, $R_{12}$, and $R_{18}$ are independently selected from the group consisting of amino-C$_3$-alkyloxy; amino-C$_3$-alkyl-carboxy; C$_8$-alkylamino-C$_5$-alkyl; C$_8$-alkoxy-carbonyl-C$_4$-alkyl; C$_8$-alkyl-carbonyl-C$_4$-alkyl; di-(C$_5$-alkyl)amino-C$_5$-alkyl; C$_{13}$-alkylamino-C$_5$-alkyl; C$_6$-alkoxy-carbonyl-C$_4$-alkyl; C$_6$-alkyl-carboxy-C$_4$-alkyl; and C$_{16}$-alkylamino-C$_5$-alkyl.

In some embodiments, m, n, and p are each 1 and q is 0.

In some embodiments, the CSA, or pharmaceutically acceptable salts thereof of Formula (I) can be also represented by Formula (III):

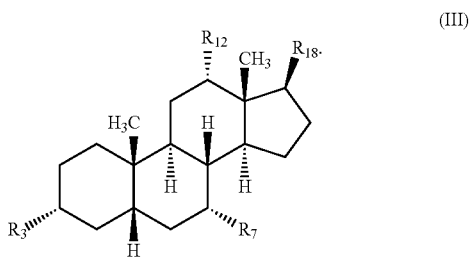

(III)

In some embodiments, the CSA, or a pharmaceutically acceptable salt thereof, is:

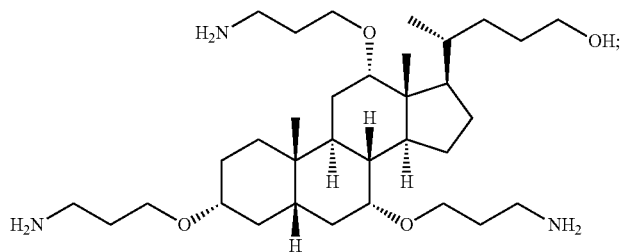

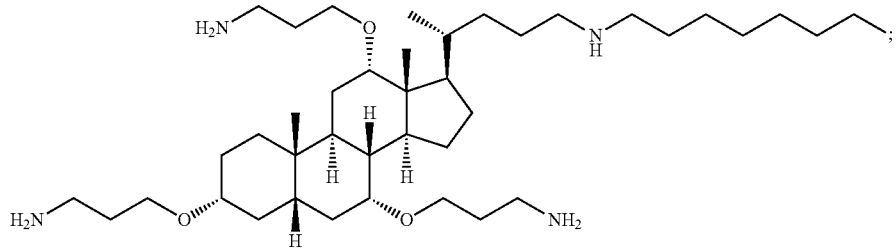

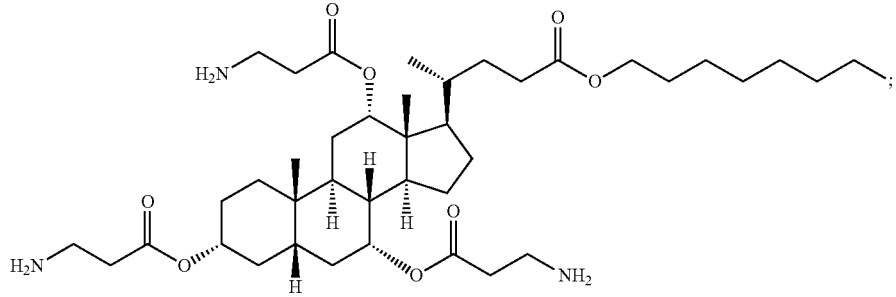

-continued
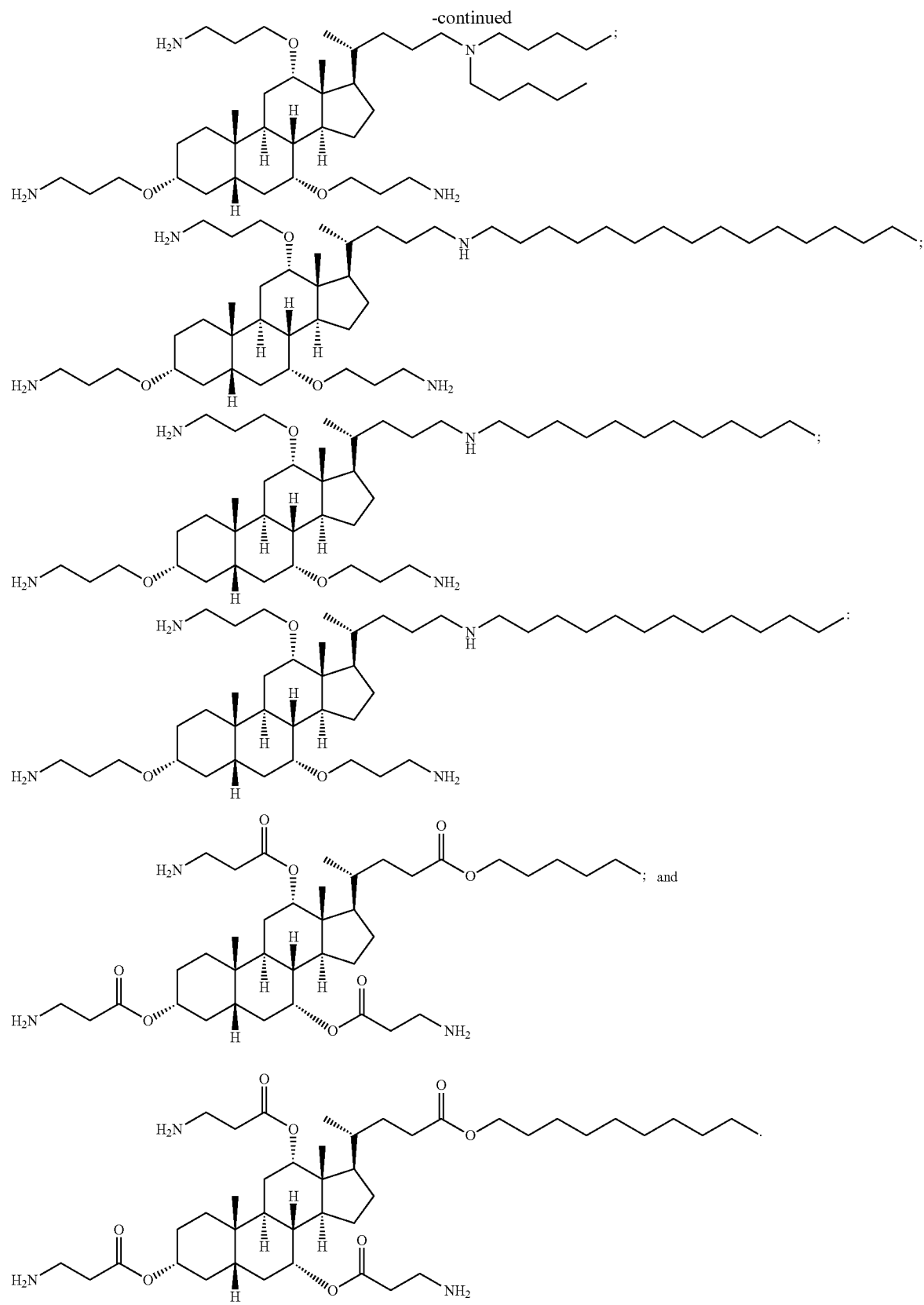
In some embodiments, the CSA, or a pharmaceutically acceptable salt thereof, is In other embodiments, the CSA, or a pharmaceutically acceptable salt thereof, is

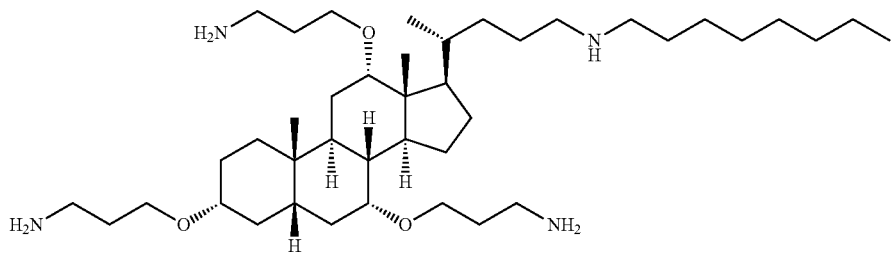

In other embodiments, the CSA, or a pharmaceutically acceptable salt thereof, is

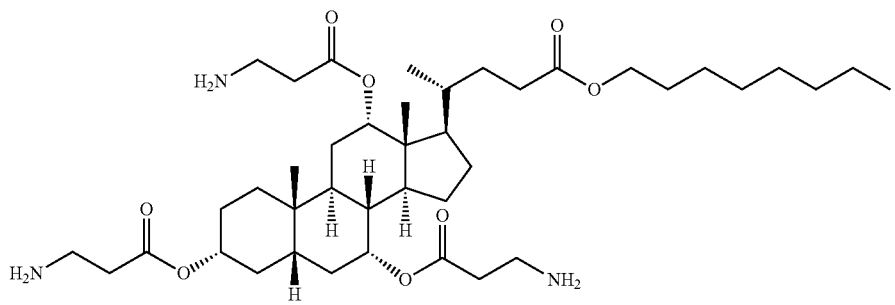

In other embodiments, the CSA, or a pharmaceutically acceptable salt thereof, is

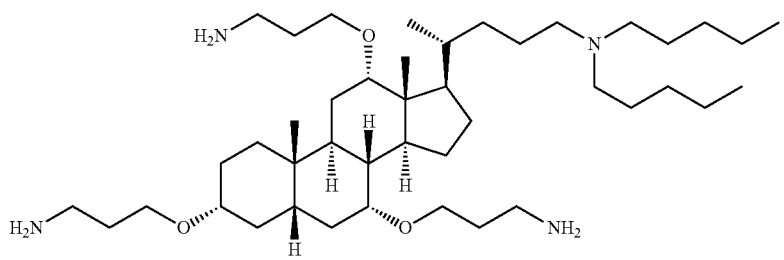

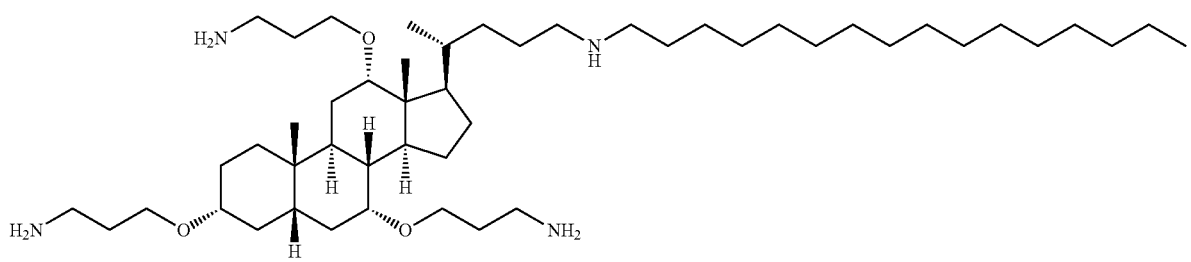

Pharmaceutically Acceptable Salts

The compounds and compositions disclosed herein are optionally prepared as pharmaceutically acceptable salts. The term "pharmaceutically acceptable salt" as used herein is a broad term, and is to be given its ordinary and customary meaning to a skilled artisan (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid, propionic acid, glycolic acid, pyruvic acid, malonic acid, maleic acid, fumaric acid, trifluoroacetic acid, benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, $C_1$-$C_7$ alkylamine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

In some embodiments, the pharmaceutically acceptable salt is a hydrochloride salt. In some embodiments, the pharmaceutically acceptable salt is a mono-hydrochloride salt, a di-hydrochloride salt, a tri-hydrochloride salt, or a tetra-hydrochloride salt.

Co-administration:

As used herein, "co-administration" means concurrently or administering one substance followed by beginning the administration of a second substance within 24 hours, 20 hours, 16 hours, 12 hours, 8 hours, 4 hours, 1 hour, 30 minutes, 15 minutes, 5 minutes, 1 minute, a range bounded by any two of the aforementioned numbers, and/or about any of the aforementioned numbers.

In some embodiments, one or more CSAs are co-administered. In other embodiments, the co-administration of CSAs accounts for their therapeutic benefit. In some embodiments, co-administration is concurrent.

In some embodiments, non-CSA chemotherapeutic agents are administered to the patient. In some embodiments, the non-CSA chemotherapeutic agents are co-administered. Such chemotherapeutic agents include, but are not limited to, a regulatory agency approved chemotherapeutic agent. In some embodiments, the regulatory agency is the Food and Drug Administration (FDA).

In some embodiments, the non-CSA chemotherapeutic agent is selected from the group consisting of alkylating agents, anthracyclines, cytoskeletal disruptors, epothilones, histone deacetylase inhibitors, topoisomerase inhibitors, kinase inhibitors, monoclonal antibodies, nucleotide analogs, peptide antibiotics, platinum-based agents, retinoids, and vinca alkaloids. Such agents are known in the art, for example, actinomycin, all-trans retinoic acid, azacitidine, azathioprine, bleomycin, bortezomib, camptothecin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, irinotecan, mechlorethamine, mercaptopurine, methotrexate, mitoxantrone, oxaliplatin, paclitaxel, pemetrexed, teniposide, tioguanine, topotecan, valrubicin, vinblastine, vincristine, vindesine, and vinorelbine.

Multi-drug resistance of cancer cells can prevent successful chemotherapy. Various mechanisms of drug resistance are known, including the ABC transporters that can remove drugs from the cells. Efflux pump inhibitors can be overexpressed in cancer and contribute to drug resistance. Co-administration of the CSA therapeutic with an effective amount of an efflux pump inhibitor, such as an ABC transport inhibitor (e.g., ABCG2) is specifically contemplated. For example, human cathelicidin or other cathelicidin could be administered in conjunction with a CSA to more effectively treat drug resistance mediated by efflux pump activity, such as ABCG2, thereby sensitizing the cancer cells to chemotherapy. In addition, any other sensitizing agent could be used.

In some embodiments, one or more CSAs are co-administered to permeabilize a cell membrane. Such permeabilization can sensitize cancer cells to chemotherapy by overcoming the effect of efflux pumps and allow therapeutic levels of anti-cancer agents to accumulate in the cell. Such co-administration may allow for the use of lower doses of anti-cancer agentsm thereby minimizing adverse side effects. In some embodiments, the anti-cancer agent is also a CSA. In other embodiments, a single CSA is administered and responsible for both anti-cancer and cell permeabilization effects.

Many cancer therapies are also immunosuppressive, and a common side effect of existing cancer therapies is infection. In some embodiments, one or more CSAs are co-administered to prevent or minimize infections during cancer treatment. Such action may be in addition to other beneficial actions against the cancer cells. In some embodiments, one or more CSAs are co-administered such that the effect is upregulation of the patient's immune system, thereby allowing the patient to counteract cancer indirectly from the administration of the CSA. In some embodiments, one or more CSAs are co-administered such that the CSAs are not directly toxic to cancer cells but improve the patient's immune status to help the patient counteract cancer and/or also help prevent metastases. In some embodiments, the same CSA is responsible for both anti-cancer and anti-infective effects. In other embodiments, the same CSA is responsible for both anti-cancer effects and upregulation of the patient's immune system.

In some embodiments, therapeutics are administered to alleviate one or more side effects of cancer treatment. In some embodiments, the administration is concurrent. As a non-limiting example, in some embodiments, anti-nausea/vomiting medicines are administered. Such medicines are known in the art and include Alprazolam; Aprepitant; Dexamethasone; Diphenhydramine; Dolasetron; Dronabinol; Granisetron; Haloperidol; Lorazepam; Metoclopramide; Nabilone; Ondansetron; Olanzapine; Palonosetron; Prochlorperazine; and Promethazine.

In some embodiments, therapeutics are administered to alleviate one or more symptoms of cancer. In some embodiments, the administration is concurrent. Non-limiting examples of symptoms include pain, loss of appetite, and depression. Medicines that alleviate these symptoms are known in the art and include, non-opioids such as acetaminophen, aspirin, and ibuprofen; opioids such as morphine, fentanyl, hydromorphone, oxycodone, and codeine; steroids such as prednisone and dexamethasone; and, for tingling or burning pain, antidepressants such as amitriptyline, nortriptyline, and desipramine and anti-convulsants such as carbamazepine, gabapentin, and phenytoin.

Some embodiments are directed to the use of companion diagnostics to identify an appropriate treatment for the patient. A companion diagnostic is an in vitro diagnostic test or device that provides information that is essential for the safe and effective use of a corresponding therapeutic product. Such tests or devices can identify patients likely to be at risk for adverse reactions as a result of treatment with a particular therapeutic product. Such tests or devices can also monitor responsiveness to treatment (or estimate responsiveness to possible treatments). Such monitoring may include schedule, dose, discontinuation, or combinations of therapeutic agents. In some embodiments, the CSA is selected by measuring a biomarker in the patient. The term biomarker includes, but is not limited to, genetic regulation, protein levels, RNA levels, and cellular responses such as cytotoxicity. In some embodiments, one or more chemotherapeutic agents are selected by subjecting a sample from the patient to a companion diagnostic device. In some embodiments, the sample is a tissue sample. In other embodiments, the tissue sample is representative of the cancer to be treated. In some embodiments, the tissue sample contains a portion of the cancer to be treated. In some embodiments, the tissue sample is not cancerous.

Pharmaceutical Compositions

While it is possible for the compounds described herein to be administered alone, it may be preferable to formulate the compounds as pharmaceutical compositions. As such, in yet another aspect, pharmaceutical compositions useful in the methods and uses of the disclosed embodiments are provided. More particularly, the pharmaceutical compositions described herein may be useful, inter alia, for treating or preventing a bone disease and/or a broken bone. A pharmaceutical composition is any composition that may be administered in vitro or in vivo or both to a subject in order to treat or ameliorate a condition. In a preferred embodiment, a pharmaceutical composition may be administered in vivo. A subject may include one or more cells or tissues, or organisms. In some exemplary embodiments, the subject is an animal. In some embodiments, the animal is a mammal. The mammal may be a human or primate in some embodiments. A mammal includes any mammal, such as by way of non-limiting example, cattle, pigs, sheep, goats, horses, camels, buffalo, cats, dogs, rats, mice, and humans.

As used herein the terms "pharmaceutically acceptable" and "physiologically acceptable" mean a biologically compatible formulation, gaseous, liquid or solid, or mixture thereof, which is suitable for one or more routes of administration, in vivo delivery, or contact. A formulation is compatible in that it does not destroy activity of an active ingredient therein (e.g., a CSA), or induce adverse side effects that far outweigh any prophylactic or therapeutic effect or benefit.

In an embodiment, the pharmaceutical compositions may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5.0 to about pH 8. More particularly, the pharmaceutical compositions may comprise a therapeutically or prophylactically effective amount of at least one compound as described herein, together with one or more pharmaceutically acceptable excipients. Optionally, the pharmaceutical compositions may comprise a combination of the compounds described herein, or may include a second active ingredient useful in the treatment or prevention of bacterial infection (e.g., anti-bacterial or anti-microbial agents).

Formulations, e.g., for parenteral or oral administration, are most typically solids, liquid solutions, emulsions or suspensions, while inhalable formulations for pulmonary administration are generally liquids or powders, with powder formulations being generally preferred. A preferred pharmaceutical composition may also be formulated as a lyophilized solid that is reconstituted with a physiologically compatible solvent prior to administration. Alternative pharmaceutical compositions may be formulated as syrups, creams, ointments, tablets, and the like.

Compositions may contain one or more excipients. Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions described herein may be formulated in any form suitable for the intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as cross-linked povidone, maize starch, or alginic acid; binding agents, such as povidone, starch, gelatin or acacia; and lubricating agents, such as magnesium stearate, stearic acid or talc.

Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions may be formulated as suspensions comprising a compound of the embodiments in admixture with at least one pharmaceutically acceptable excipient suitable for the manufacture of a suspension.

In yet another embodiment, pharmaceutical compositions may be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methylcellulose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); polysaccharides and polysaccharide-like compounds (e.g. dextran sulfate); glycoaminoglycans and glycosaminoglycan-like compounds (e.g., hyaluronic acid); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions may also be in the form of oil-in water emulsions. The oily phase may be a vegetable oil, such as olive oil or *arachis* oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions may be in the form of a sterile injectable preparation, such as a sterile injectable aqueous emulsion or oleaginous suspension. This emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol.

The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids such as oleic acid may likewise be used in the preparation of injectables.

To obtain a stable water-soluble dose form of a pharmaceutical composition, a pharmaceutically acceptable salt of a compound described herein may be dissolved in an aqueous solution of an organic or inorganic acid, such as 0.3 M solution of succinic acid, or more preferably, citric acid. If a soluble salt form is not available, the compound may be dissolved in a suitable co-solvent or combination of co-solvents. Examples of suitable co-solvents include alcohol, propylene glycol, polyethylene glycol 300, polysorbate 80, glycerin and the like in concentrations ranging from about 0 to about 60% of the total volume. In one embodiment, the active compound is dissolved in DMSO and diluted with water.

The pharmaceutical composition may also be in the form of a solution of a salt form of the active ingredient in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, and complexation.

Many therapeutics have undesirably short half-lives and/or undesirable toxicity. Thus, the concept of improving half-life or toxicity is applicable to treatments and fields other than cancer. Pharmaceutical compositions can be prepared, however, by complexing the therapeutic with a biochemical moiety to improve such undesirable properties. Proteins are a particular biochemical moiety that may be complexed with a CSA for administration in a wide variety of applications. In some embodiments, one or more CSAs are complexed with a protein for the treatment of infection. In other embodiments, one or more CSAs are complexed with a protein for the treatment of cancer. In some embodiments, one or more CSAs are complexed with a protein to increase the CSA's half-life. In other embodiments, one or more CSAs are complexed with a protein to decrease the CSA's toxicity. Albumin is a particularly preferred protein for complexation with a CSA. In some embodiments, the albumin is fat-free albumin.

With respect to the CSA therapeutic, the biochemical moiety for complexation can be added to the pharmaceutical composition as 0.25, 0.5, 0.75, 1, 1.5, 2, 2.5, 3, 3.5, 4, 4.5, 5, 10, 20, 50, or 100 weight equivalents, or a range bounded by any two of the aforementioned numbers, or about any of the numbers. In some embodiments, the weight ratio of albumin to CSA is about 18:1 or less, such as about 9:1 or less. In some embodiments, the CSA is coated with albumin.

Alternatively, or in addition, non-biochemical compounds can be added to the pharmaceutical compositions to reduce the toxicity of the therapeutic and/or improve the half-life. Such an application is not limited to anti-cancer treatment, but instead has wide applicability to various forms of treatment, such as treating infections or cancer. Suitable amounts and ratios of an additive that can improve toxicity can be determined via a cellular assay. With respect to the CSA therapeutic, toxicity reducing compounds can be added to the pharmaceutical composition as 0.25, 0.5, 0.75, 1, 1.5, 2, 2.5, 3, 3.5, 4, 4.5, 5, 10, 20, 50, or 100 weight equivalents, or a range bounded by any two of the aforementioned numbers, or about any of the numbers. In some embodiments, the toxicity reducing compound is a cocoamphodiacetate such as Miranol® (disodium cocoamphodiacetate). In other embodiments, the toxicity reducing compound is an amphoteric surfactant. In some embodiments, the toxicity reducing compound is a surfactant. In other embodiments, the molar ratio of cocoamphodiacetate to CSA is between about 8:1 and 1:1, preferably about 4:1. In some embodiments, the toxicity reducing compound is allantoin.

In one embodiment, the compounds described herein may be formulated for oral administration in a lipid-based formulation suitable for low solubility compounds. Lipid-based formulations can generally enhance the oral bioavailability of such compounds.

As such, a pharmaceutical composition comprises a therapeutically or prophylactically effective amount of a compound described herein, together with at least one pharmaceutically acceptable excipient selected from the group consisting of-medium chain fatty acids or propylene glycol esters thereof (e.g., propylene glycol esters of edible fatty acids such as caprylic and capric fatty acids) and pharmaceutically acceptable surfactants such as polyoxyl 40 hydrogenated castor oil.

In an alternative preferred embodiment, cyclodextrins may be added as aqueous solubility enhancers. Preferred cyclodextrins include hydroxypropyl, hydroxyethyl, glucosyl, maltosyl and maltotriosyl derivatives of $\alpha$-, $\beta$-, and $\gamma$-cyclodextrin. A particularly preferred cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprises about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound of the embodiments in the composition.

In some exemplary embodiments, a CSA comprises a multimer (e.g., a dimer, trimer, tetramer, or higher order polymer). In some exemplary embodiments, the CSAs can be incorporated into pharmaceutical compositions or formulations. Such pharmaceutical compositions/formulations are useful for administration to a subject, in vivo or ex vivo. Pharmaceutical compositions and formulations include carriers or excipients for administration to a subject.

Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

A pharmaceutical composition and/or formulation contains a total amount of the active ingredient(s) sufficient to achieve an intended therapeutic effect.

The term "packaging material" refers to a physical structure housing one or more components of the kit. The packaging material can maintain the components sterilely, and can be made of material commonly used for such purposes (e.g., paper, corrugated fiber, glass, plastic, foil, ampules, vials, tubes, etc.). A kit can contain a plurality of components, e.g., two or more compounds alone or in combination with an osteogenesis agent or treatment or drug, optionally sterile.

A kit optionally includes a label or insert including a description of the components (type, amounts, doses, etc.), instructions for use in vitro, in vivo, or ex vivo, and any other components therein. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., floppy diskette, hard disk, ZIP disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

One of ordinary skill in the art to which these exemplary embodiments belong will understand that the compositions may be administered in numerous ways. For example, administration may mean simply applying the compositions to a bone directly. In some exemplary embodiments, administration may be enteral, parenteral, or topical. Other exemplary routes of administration for contact or in vivo delivery which a compound can optionally be formulated include inhalation, respiration, intubation, intrapulmonary instillation, oral (buccal, sublingual, mucosal), intrapulmonary, rectal, vaginal, intrauterine, intradermal, topical, dermal, parenteral (e.g., subcutaneous, intramuscular, intravenous, intradermal, intraocular, intratracheal and epidural), intranasal, intrathecal, intraarticular, intracavity, transdermal, iontophoretic, ophthalmic, optical (e.g., corneal), intraglandular, intraorgan, and/or intralymphatic.

The delivery forms can be homogeneous, e.g., forms in which the composition is in solution, or heterogeneous, e.g., forms in which the composition is contained within liposomes or microspheres. The forms can produce an immediate effect, and can alternatively, or additionally, produce an extended effect. For example, liposomes, or microspheres, or other similar means of providing an extended release of the composition, can be used to extend the period during which the composition is exposed to the targeted area; non-encapsulated compositions can also be provided for an immediate effect.

In some embodiments, the composition or method includes administering a CSA from a pharmaceutically acceptable device(s) such as bandages, surgical dressings, gauzes, adhesive strips, surgical staples, clips, hemostats, intrauterine devices, sutures, trocars, catheters, tubes, and implants. In some embodiments, the implant is a pill, pellet, rod, screw, wafer, disc, and/or tablet. The devices can deliver the composition to a targeted area for a desired period of time. In some exemplary embodiments, the composition may be incorporated into a medical device coating. In some embodiments, the coating contains 0.1 weight %, 1 weight %, 5 weight %, 10 weight %, 15 weight %, 20 weight %, 25 weight %, 50 weight %, about any of the aforementioned numbers, and/or a range bounded by any two of the aforementioned numbers.

Devices according to the disclosure can be prepared according to known methods, and can include, or be made from, polymeric material. In some instances, the polymeric material will be an absorbable material and in other instances, a non-absorbable material, or in other instances a resorbable material. Devices can, of course, include absorbable, non-absorbable, resorbable materials, and combinations thereof.

Absorbable materials can be synthetic materials and non-synthetic materials. Absorbable synthetic materials include, but are not limited to, cellulosic polymers, glycolic acid polymers, methacrylate polymers, ethylene vinyl acetate polymers, ethylene vinyl alcohol copolymers, polycaptrolactam, polyacetate, copolymers of lactide and glycolide, polydioxanone, polyglactin, poliglecaprone, polyglyconate, polygluconate, and combinations thereof. Absorbable non-synthetic materials include, but are not limited to, catgut, cargile membrane, fascia lata, gelatin, collagen, and combinations thereof.

Nonabsorbable synthetic materials include, but are not limited to nylons, rayons, polyesters, polyolefins, and combinations thereof. Non-absorbable non-synthetic materials include, but are not limited to, silk, dermal silk, cotton, linen, and combinations thereof.

Combinations of the foregoing devices and carriers/vehicles are also envisioned. For example, a CSA gel or ointment can be impregnated into a bandage or wound dressing for delivery of the CSA to a targeted location. As another example, an implantable absorbable device can be loaded with a CSA material and release the CSA from the device over a desired period. Sustained or controlled release formulations, compositions, or devices can be used. A desired period of delivery can be, for example, at least about 2, 3, 6, 10, 12, 18, or 24 hours, or 1, 2, 4, 8, 12, 20, or 30 days, or 1, 2, 3, 4, 5, 6, or more months, and any value in between. The physical form used to deliver the CSA is not critical and the choice or design of such devices is well within the level of skill of one in the art.

It may be desirable to provide for other conditions in the practice of the present methods. For example, it may be desirable to ensure that the target region is sufficiently oxygenated; generally, it is sufficient that atmospheric oxygen be present. It also may be desirable to maintain a desired level of moisture and a particular temperature; in some embodiments, a warm, moist environment is desirable. While not required, it may also be desirable to establish or maintain a sterile environment.

Additionally, it may be desirable to include other therapeutically beneficial agents in the formulation. For example, the vehicles or carriers may also include humectants or moisturizers to maintain a desired moisture level in the treated area. Other possibilities include drugs such as anesthetics or antibiotics, which provide other desired effects. Again, known to serve.

Dosages

The formulations may, for convenience, be prepared or provided as a unit dosage form. Preparation techniques include bringing into association the active ingredient (e.g., CSA) and a pharmaceutical carrier(s) or excipient(s). In general, formulations are prepared by uniformly and intimately associating the active ingredient with liquid carriers or finely divided solid carriers or both, and then, if necessary, shaping the product. For example, a tablet may be made by compression or molding. Compressed tablets may be prepared by compressing, in a suitable machine, an active ingredient (e.g., a CSA) in a free-flowing form such as a powder or granules, optionally mixed with a binder, lubricant, inert diluent, preservative, surface-active or dispersing agent. Molded tablets may be produced by molding, in a suitable apparatus, a mixture of powdered compound (e.g., CSA) moistened with an inert liquid diluent. The tablets may optionally be coated or scored and may be formulated so as to provide a slow or controlled release of the active ingredient therein.

Compounds (e.g., CSAs), including pharmaceutical formulations can be packaged in unit dosage forms for ease of administration and uniformity of dosage. A "unit dosage form" as used herein refers to a physically discrete unit suited as unitary dosages for the subject to be treated; each unit containing a predetermined quantity of compound optionally in association with a pharmaceutical carrier (excipient, diluent, vehicle or filling agent) which, when administered in one or more doses, is calculated to produce a desired effect (e.g., prophylactic or therapeutic effect or benefit). Unit dosage forms can contain a daily dose or unit, daily sub-dose, or an appropriate fraction thereof, of an administered compound (e.g., CSA). Unit dosage forms also include, for example, capsules, troches, cachets, lozenges, tablets, ampules and vials, which may include a composition in a freeze-dried or lyophilized state; a sterile liquid carrier, for example, can be added prior to administration or delivery in vivo. Unit dosage forms additionally include, for example, ampules and vials with liquid compositions disposed therein. Unit dosage forms further include compounds for transdermal administration, such as "patches" that contact with the epidermis of the subject for an extended or brief period of time. The individual unit dosage forms can be included in multi-dose kits or containers. Pharmaceutical formulations can be packaged in single or multiple unit dosage forms for ease of administration and uniformity of dosage.

Compounds (e.g., CSAs) can be administered in accordance with the methods at any frequency as a single bolus or multiple dose e.g., one, two, three, four, five, or more times hourly, daily, weekly, monthly, or annually or between about 1 to 10 days, weeks, months, or for as long as appropriate. Exemplary frequencies are typically from 1-7 times, 1-5 times, 1-3 times, 2-times or once, daily, weekly or monthly. Timing of contact, administration ex vivo or in vivo delivery can be dictated by the infection, pathogenesis, symptom, pathology or adverse side effect to be treated. For example, an amount can be administered to the subject substantially contemporaneously with, or within about 1-60 minutes or hours of the onset of a symptom or adverse side effect, pathogenesis, or vaccination. Long-acting pharmaceutical compositions may be administered twice a day, once a day, once every two days, three times a week, twice a week, every 3 to 4 days, or every week depending on half-life and clearance rate of the particular formulation. For example, in an embodiment, a pharmaceutical composition contains an amount of a compound as described herein that is selected for administration to a patient on a schedule selected from: twice a day, once a day, once every two days, three times a week, twice a week, and once a week.

Localized delivery is also contemplated, including but not limited to delivery techniques in which the compound is implanted, injected, infused, or otherwise locally delivered. Localized delivery is characterized by higher concentrations of drug at the site of desired action (e.g., the tumor or organ to be treated) versus systemic concentrations of the drug. Well-known localized delivery forms can be used, including long-acting injections; infusion directly into the site of action; depot delivery forms; controlled or sustained delivery compositions; transdermal patches; infusion pumps; and the like. The CSA can further be incorporated into a biodegradable or bioerodible material or be put into or on a medical device.

Doses may vary depending upon whether the treatment is therapeutic or prophylactic, the onset, progression, severity, frequency, duration, probability of or susceptibility of the symptom, the type pathogenesis to which treatment is directed, clinical endpoint desired, previous, simultaneous or subsequent treatments, general health, age, gender or race of the subject, bioavailability, potential adverse systemic, regional or local side effects, the presence of other disorders or diseases in the subject, and other factors that will be appreciated by the skilled artisan (e.g., medical or familial history). Dose amount, frequency or duration may be increased or reduced, as indicated by the clinical outcome desired, status of the infection, symptom or pathology, any adverse side effects of the treatment or therapy. The skilled artisan will appreciate the factors that may influence the dosage, frequency and timing required to provide an amount sufficient or effective for providing a prophylactic or therapeutic effect or benefit. The exact dosage will be determined by the practitioner, in light of factors related to the subject that requires treatment. Dosage and administration are adjusted to provide sufficient levels of the active agent(s) or to maintain the desired effect. It will be appreciated that treatment as described herein includes preventing a disease, ameliorating symptoms, slowing disease progression, reversing damage, or curing a disease.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The systemic daily dosage regimen for an adult human patient may be, for example, an oral dose of between 0.01 mg and 3000 mg of the active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years. Doses tailored for particular types of cancers or particular patients can be selected based, in part, on the $GI_{50}$, TGI, and $LC_{50}$ values set forth in the Examples that follow.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or conditions.

Dosage amount and interval may be adjusted individually to provide plasma levels of the active moiety which are sufficient to maintain the modulating effects, or minimal effective concentration (MEC). For example, therapeutic dosages may result in plasma levels of 0.05 µg/mL, 0.1 µg/mL, 0.5 µg/mL, 1 µg/mL, 5 µg/mL, 10 µg/mL, 15 µg/mL, 20 µg/mL, g/mL, 30 µg/mL, 35 µg/mL, 40 µg/mL, 45 µg/mL, 50 µg/mL, 55 µg/mL, 60 µg/mL, 65 g/mL, 70 µg/mL, 75 µg/mL, 80 µg/mL, 85 µg/mL, 90 µg/mL, 95 µg/mL, 100 µg/mL, a range bounded by any two of the aforementioned numbers, or about any of the aforementioned numbers and ranges. In some embodiments, the therapeutic dose is sufficient to establish plasma levels in the range of about 0.1 µg/mL to about 10 µg/mL. In other embodiments, the therapeutic dose is sufficient to establish plasma levels in the range of 1 g/mL to 20 µg/mL. The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

As described herein, the methods of the embodiments also include the use of a compound or compounds as described herein together with one or more additional therapeutic agents for the treatment of disease conditions. Thus, for example, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

EXAMPLES

Synthesis of CSAs:

Compounds described herein can be prepared by known methods, such as those disclosed in U.S. Pat. No. 6,350,738, which are incorporated herein by reference. A skilled artisan will readily understand that minor variations of starting materials and reagents may be utilized to prepare known and novel cationic steroid antimicrobials. For example, the preparation of CSA-13 disclosed in U.S. Pat. No. 6,350,738 (compound 133) can be used to prepare CSA-92 by using hexadecylamine rather than octyl amine as disclosed. Schematically, for example, the preparation of certain compounds can be accomplished as follows:

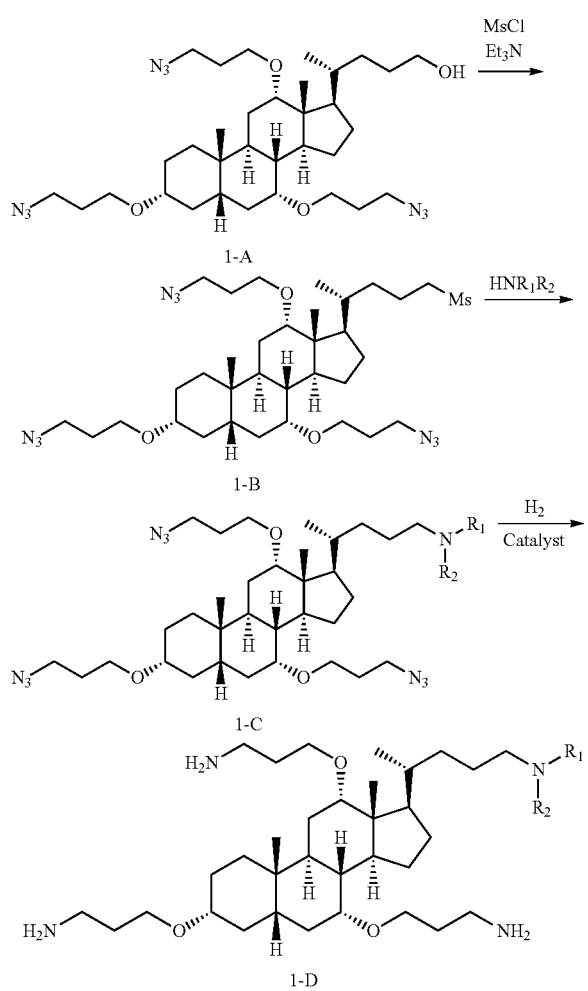

1-A

1-B

1-C

1-D

As shown above, compound 1-A is converted to the mesylate, compound 1-B using known conditions. Treatment of compound 1-B with a secondary amine, such as $HNR_1R_2$, results in the formation of compound 1-C, whose azido functional groups are reduced with hydrogen gas in the presence of a suitable catalyst to afford compound 1-D. Suitable catalysts include Palladium on Carbon and Lindlar catalyst. The reagent $HNR_1R_2$ is not particularly limited under this reaction scheme. For example, when $R_1$ is hydrogen and $R_2$ is a $C_8$-alkyl, CSA-13 is obtained from the synthesis. When $R_1$ is hydrogen and $R_2$ is a $C_{16}$-alkyl, CSA-92 is obtained from the synthesis. When $R_1$ and $R_2$ are both $C_5$-alkyl, CSA-90 is obtained from the synthesis.

Anti-cancer Activity:

The antiproliferative activity of compounds were determined in the National Cancer Institute (NCI) screen (Drug. Dev. Res. 1995, 34, 91-109; J. Natl. Cancer Inst. 1990, 82, 1107-1112; Drug Dev. Res. 1995, 34, 91-109). For certain compounds, cells of approximately 60 different human cancer cell lines were incubated for 48 hours with five 10-fold dilutions of the tested compounds starting from 100 μM and then treated with sulforhodamine B dye. For other compounds, cells of approximately 60 different human cancer cell lines were incubated for 48 hours with a concentration of 10 μM test compound. The ratios of recorded optical densities relative to that of the control were plotted as a function of the common logarithm of the tested compound concentrations or growth percent (for single concentration tests). The interpolation between the points located above and below the 50% percentage growth provided 50% growth inhibition ($GI_{50}$) values. Total growth inhibition (TGI) and 50% lethal concentrations ($LC_{50}$) were also calculated using reported methods. A "–" means not tested and/or not-determined.

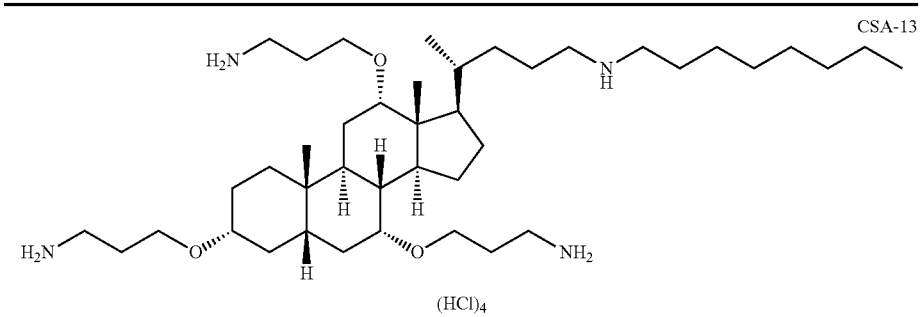

CSA-13

| Panel/Cell Line | $GI_{50}$ μM | TGI μM | $LC_{50}$ μM |
|---|---|---|---|
| Leukemia | | | |
| K-562 | 1.04 | 2.47 | — |
| MOLT-4 | 1.25 | 2.93 | — |
| RPMI-8226 | 0.266 | 0.911 | — |
| SR | 0.272 | 2.29 | — |
| Non-Small Cell Lung Cancer | | | |
| A549/ATCC | 2.01 | 9.33 | 45.9 |
| EKVX | 1.32 | 3.38 | 8.62 |
| HOP-62 | 0.806 | 2.96 | 9.74 |
| HOP-92 | 0.408 | 21.2 | >100 |
| NCI-H226 | 2.22 | 12.8 | 66.8 |

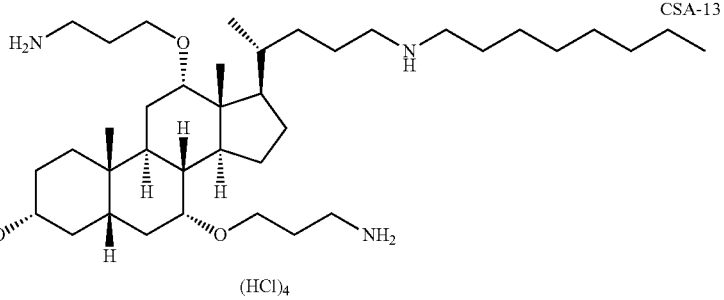
CSA-13
(HCl)₄
| Panel/Cell Line | GI$_{50}$ μM | TGI μM | LC$_{50}$ μM |
|---|---|---|---|
| NCI-H23 | 1.24 | 3.12 | 7.87 |
| NCI-H322M | 1.36 | 9.31 | >100 |
| NCI-H460 | 1.21 | 3.92 | 15.5 |
| NCI-H522 | 2.59 | 10.5 | >100 |
| Colon Cancer | | | |
| COLO 205 | 1.27 | 3.02 | — |
| HCC-2998 | 1.51 | 3.98 | 13.3 |
| HCT-116 | 0.87 | 2.61 | 7.25 |
| HCT-15 | 2.63 | 14.8 | 63.9 |
| HT29 | 1.11 | 5.31 | 34.0 |
| KM12 | 0.586 | 2.76 | — |
| SW-620 | 1.16 | 2.67 | — |
| CNS Cancer | | | |
| SF-268 | 1.50 | 3.70 | 9.14 |
| SF-295 | 0.496 | 2.66 | 24.0 |
| SF-539 | 0.318 | 1.41 | 4.89 |
| SNB-19 | 1.49 | 5.05 | 89.3 |
| SNB-75 | 1.76 | 5.93 | 57.2 |
| U251 | 1.37 | 3.05 | 6.81 |
| Melanoma | | | |
| LOX IMVI | 0.378 | 1.73 | — |
| MALME-3M | 1.76 | 3.88 | — |
| M14 | 1.18 | 3.52 | 12.6 |
| SK-MEL-2 | 4.51 | >100 | >100 |
| SK-MEL-28 | 0.291 | 1.27 | 5.46 |
| SK-MEL-5 | 0.504 | 1.92 | — |
| UACC-257 | 2.71 | 9.00 | 97.9 |
| UACC-62 | 0.482 | 2.29 | 9.43 |
| Ovarian Cancer | | | |
| IGROV1 | 1.44 | 3.54 | 8.67 |
| OVCAR-3 | 2.24 | 14.8 | 88.0 |
| OVCAR-4 | 5.51 | 25.2 | 83.0 |
| OVCAR-5 | 1.55 | 9.44 | 58.4 |
| OVCAR-8 | 1.64 | 4.01 | 9.82 |
| SK-OV-3 | 3.45 | 16.3 | 93.1 |
| Renal Cancer | | | |
| 786-0 | 0.837 | 2.26 | 5.40 |
| ACHN | 1.48 | 3.68 | 9.17 |
| CAKI-1 | 2.05 | 10.6 | 68.0 |
| RXF 393 | 1.54 | 15.6 | >100 |
| SN12C | 0.571 | 3.55 | 27.0 |
| TK-10 | 0.974 | 4.70 | >100 |
| UO-31 | 1.49 | — | >100 |
| Prostate Cancer | | | |
| PC-3 | 3.74 | >100 | >100 |
| DU-145 | 1.14 | 2.35 | 4.85 |
| Breast Cancer | | | |
| MCF7 | 1.63 | 3.09 | 5.85 |
| NCI-ADR-RES | 1.83 | 5.33 | 36.5 |
| MDA-MB-231/ATCC | 0.422 | 4.08 | >100 |
| HS 578T | 0.854 | 2.35 | — |
| MDA-MB-435 | 0.318 | 1.46 | 5.68 |
| BT-549 | 1.07 | 3.28 | >100 |
| T-47D | 1.92 | 7.13 | >100 |

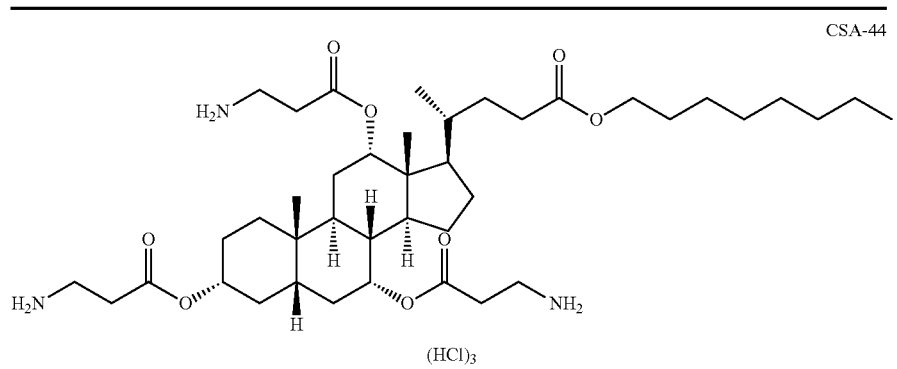
CSA-44
(HCl)₃
| Panel/Cell Line | Growth Percent |
|---|---|
| Leukemia | |
| CCRF-CEM | −37.46 |
| HL-60(TB) | 43.69 |
| K-562 | −74.53 |
| MOLT-4 | 26.15 |
| RPMI-8226 | 77.75 |
| SR | −12.92 |
| Non-Small Cell Lung Cancer | |
| A549/ATCC | 81.31 |
| HOP-62 | 37.66 |
| HOP-92 | 40.75 |
| NCI-H226 | 89.76 |
| NCI-H23 | 90.31 |
| NCI-H322M | 71.42 |
| NCI-H460 | 73.70 |
| NCI-H522 | 10.80 |
| Colon Cancer | |
| COLO 205 | 66.35 |
| HCC-2998 | 84.20 |
| HCT-116 | 49.30 |
| HCT-15 | 101.79 |
| HT29 | 39.62 |
| KM12 | 77.75 |
| SW-620 | 20.01 |
| CNS Cancer | |
| SF-268 | 69.72 |
| SF-539 | 56.26 |
| SNB-19 | 115.74 |
| SNB-75 | 63.88 |
| Melanoma | |
| LOX IMVI | 63.17 |
| MALME-3M | 67.83 |
| M14 | 84.43 |
| MDA-MB-435 | 74.13 |
| SK-MEL-2 | 126.21 |
| SK-MEL-28 | 58.43 |
| SK-MEL-5 | 96.98 |
| UACC-62 | 103.61 |
| Ovarian Cancer | |
| IGROV1 | 77.22 |
| OVCAR-3 | 107.53 |
| OVCAR-4 | 75.66 |
| OVCAR-5 | 92.12 |
| OVCAR-8 | 69.53 |
| NCI/ADR-RES | 100.83 |
| SK-OV-3 | 90.91 |
| Renal Cancer | |
| 786-0 | 99.05 |
| A498 | 130.78 |
| ACHN | 96.19 |
| CAKI-1 | 107.94 |
| RXF 393 | 108.72 |

CSA-44
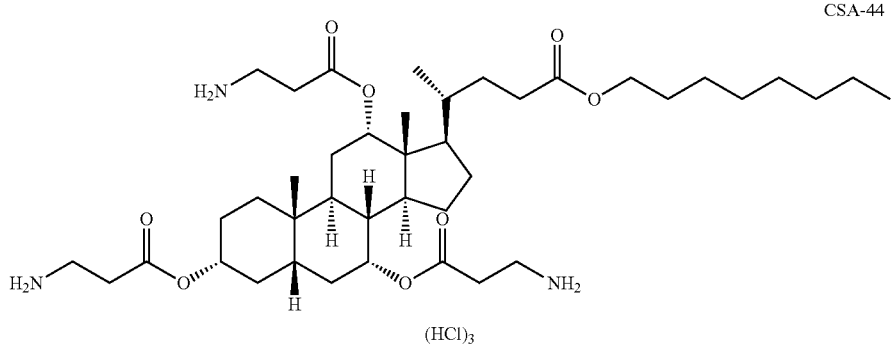
(HCl)₃
| Panel/Cell Line | Growth Percent |
|---|---|
| SN12C | 77.59 |
| TK-10 | 135.94 |
| UO-31 | 104.69 |
| Prostate Cancer | |
| PC-3 | 87.30 |
| DU-145 | 74.35 |
| Breast Cancer | |
| MCF7 | 10.84 |
| MDA-MB-231/ATCC | 69.26 |
| HS 578T | 79.51 |
| BT-549 | 124.30 |
| T-47D | 88.83 |
| MDA-MB-468 | 3.95 |
CSA-90
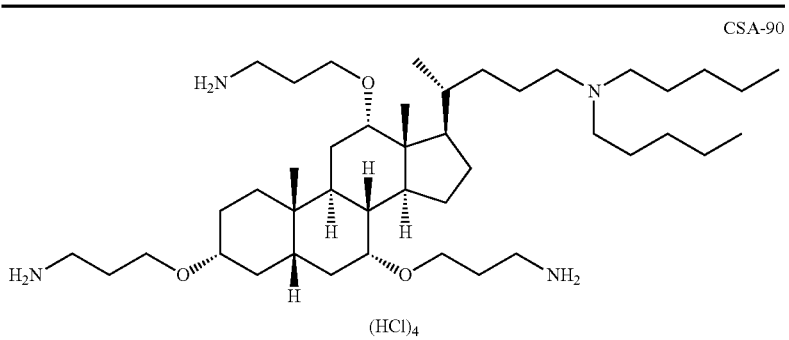
(HCl)₄
| Panel/Cell Line | Growth Percent |
|---|---|
| Leukemia | |
| CCRF-CEM | 15.29 |
| HL-60(TB) | −16.84 |
| K-562 | −19.42 |
| MOLT-4 | 41.11 |
| RPMI-8226 | −17.73 |
| SR | 19.21 |
| Non-Small Cell Lung Cancer | |
| A549/ATCC | 55.21 |
| HOP-62 | 48.28 |
| HOP-92 | 50.03 |
| NCI-H226 | 75.25 |
| NCI-H23 | 49.16 |
| NCI-H322M | 24.61 |
| NCI-H460 | 45.20 |
| NCI-H522 | 28.85 |
| Colon Cancer | |
| COLO 205 | 52.08 |
| HCC-2998 | 59.63 |

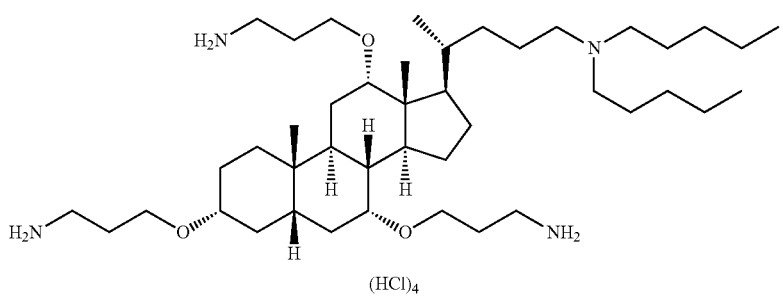
CSA-90 (HCl)$_4$
| Panel/Cell Line | Growth Percent |
|---|---|
| HCT-116 | 22.71 |
| HCT-15 | 72.31 |
| HT29 | 24.49 |
| KM12 | 22.46 |
| SW-620 | 45.90 |
| CNS Cancer | |
| SF-268 | 87.47 |
| SF-539 | −21.94 |
| SNB-19 | 61.03 |
| SNB-75 | 70.61 |
| Melanoma | |
| LOX IMVI | 3.00 |
| MALME-3M | 62.21 |
| M14 | 42.81 |
| MDA-MB-435 | −13.61 |
| SK-MEL-28 | 27.91 |
| SK-MEL-5 | 25.14 |
| UACC-62 | 13.55 |
| Ovarian Cancer | |
| IGROV1 | 29.55 |
| OVCAR-3 | 107.13 |
| OVCAR-4 | 85.16 |
| OVCAR-5 | 66.15 |
| OVCAR-8 | 55.32 |
| NCI/ADR-RES | 76.04 |
| SK-OV-3 | 93.22 |
| Renal Cancer | |
| 786-0 | 61.11 |
| A498 | 92.77 |
| ACHN | 54.72 |
| CAKI-1 | 75.81 |
| RXF 393 | 87.11 |
| SN12C | 54.27 |
| UO-31 | 65.22 |
| Prostate Cancer | |
| PC-3 | 80.53 |
| DU-145 | 76.50 |
| Breast Cancer | |
| MCF7 | 74.77 |
| MDA-MB-231/ATCC | 36.97 |
| HS 578T | 66.91 |
| BT-549 | 54.97 |
| T-47D | 68.11 |
| MDA-MB-468 | 71.06 |

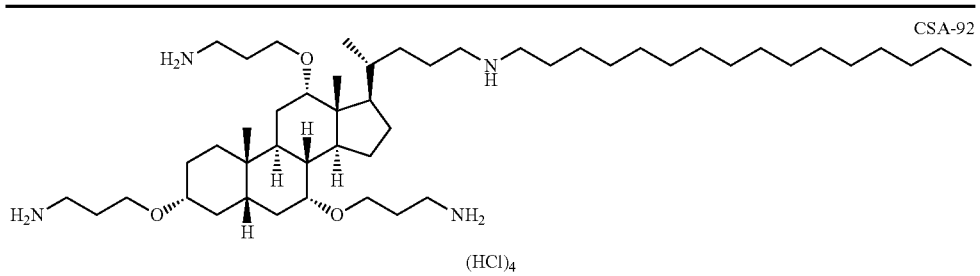

CSA-92

(HCl)₄

| Panel/Cell Line | Growth Percent |
|---|---|
| Leukemia | |
| CCRF-CEM | −45.52 |
| HL-60(TB) | 4.50 |
| K-562 | −34.68 |
| MOLT-4 | −33.70 |
| RPMI-8226 | −15.39 |
| SR | 2.63 |
| Non-Small Cell Lung Cancer | |
| A549/ATCC | −57.98 |
| HOP-62 | −49.53 |
| HOP-92 | −33.16 |
| NCI-H226 | −1.42 |
| NCI-H23 | −39.72 |
| NCI-H322M | −76.83 |
| NCI-H460 | −45.47 |
| NCI-H522 | −43.60 |
| Colon Cancer | |
| COLO 205 | −40.80 |
| HCC-2998 | −32.41 |
| HCT-116 | −16.64 |
| HCT-15 | 7.08 |
| HT29 | −40.97 |
| KM12 | −24.28 |
| SW-620 | −25.31 |
| CNS Cancer | |
| SF-268 | −38.18 |
| SF-539 | −68.05 |
| SNB-19 | −66.56 |
| SNB-75 | −64.78 |
| Melanoma | |
| LOX IMVI | −60.40 |
| MALME-3M | −60.74 |
| M14 | −28.70 |
| MDA-MB-435 | −28.31 |
| SK-MEL-28 | −64.73 |
| SK-MEL-5 | 3.14 |
| UACC-62 | −64.22 |
| Ovarian Cancer | |
| IGROV1 | −41.76 |
| OVCAR-3 | −10.46 |
| OVCAR-4 | −37.10 |
| OVCAR-5 | −3.67 |
| OVCAR-8 | −48.90 |
| NCI/ADR-RES | −60.60 |
| SK-OV-3 | −45.67 |
| Renal Cancer | |
| 786-0 | −43.08 |
| A498 | −5.88 |
| ACHN | −26.45 |
| CAKI-1 | −70.80 |
| RXF 393 | −41.21 |
| SN12C | −82.86 |
| TK-10 | −60.33 |
| UO-31 | −52.51 |
| Prostate Cancer | |
| PC-3 | −14.45 |
| DU-145 | −82.24 |

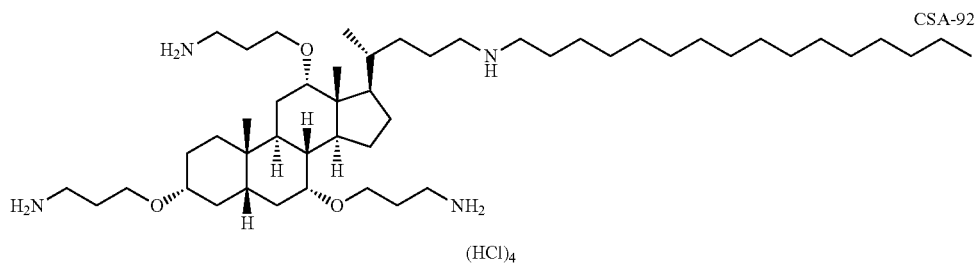

CSA-92

(HCl)$_4$

| Panel/Cell Line | Growth Percent |
|---|---|
| Breast Cancer | |
| MCF7 | −44.27 |
| MDA-MB-231/ATCC | −98.22 |
| HS 578T | −34.00 |
| BT-549 | −26.02 |
| T-47D | −20.87 |
| MDA-MB-468 | −55.21 |

CONCLUSION

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

The invention claimed is:

1. A method of therapeutically treating cancer, comprising:
    identifying a patient in need of therapeutic treatment of a cancer selected from cancer of the gastrointestinal tract, bone cancer, lung cancer, colon cancer, central nervous system (CNS) cancer, skin cancer, ovarian cancer, renal cancer, prostate cancer, breast cancer, multiple myeloma, leukemia, melanoma, basal cell carcinoma, bladder cancer, rectal cancer, lymphoma, non-Hodgkin lymphoma, endometrial cancer, pancreatic cancer, kidney cancer, or thyroid cancer; and
    administering to the patient a therapeutically effective amount of a non-isotopically labeled and radio-stable cationic steroid antimicrobial (CSA) of Formula I, or a pharmaceutically acceptable salt thereof, that is effective in reducing proliferation of cancerous cells and/or that is cytotoxic to cancerous cells:

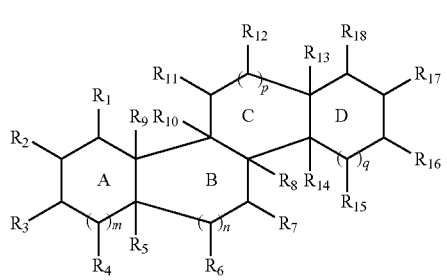

(I)

where, rings A, B, C, and D are independently saturated, or are fully or partially unsaturated, provided that at least two of rings A, B, C, and D are saturated;

m, n, p, and q are independently 0 or 1;

$R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, substituted or unsubstituted alkyl, substituted or unsubstituted hydroxyalkyl, substituted or unsubstituted alkyloxyalkyl, substituted or unsubstituted alkylcarboxyalkyl, substituted or unsubstituted alkylaminoalkyl, substituted or unsubstituted alkylaminoalkylamino, substituted or unsubstituted alkylaminoalkylamino-alkylamino, substituted or unsubstituted aminoalkyl, substituted or unsubstituted aryl, substituted or unsubstituted arylaminoalkyl, substituted or unsubstituted haloalkyl, substituted or unsubstituted alkenyl, substituted or unsubstituted alkynyl, oxo, linking group attached to a second CSA, substituted or unsubstituted aminoalkyloxy, substituted or unsubstituted aminoalkyloxyalkyl, substituted or unsubstituted aminoalkylcarboxy, substituted or unsubstituted aminoalkylaminocarbonyl, substituted or unsubstituted aminoalkyl-carboxamido, substituted or unsubstituted di(alkyl)aminoalkyl, $H_2N-HC(Q_5)-C(O)-O-$, $H_2N-HC(Q_5)-C(O)-N(H)-$, substituted or unsubstituted azidoalkyloxy, substituted or unsubstituted cyanoalkyloxy, P.G.-HN-HC($Q_5$)-C(O)-O-, substituted or unsubstituted guanidinoalkyloxy, substituted or unsubstituted quaternary ammonium alkylcarboxy, and substituted or unsubstituted guanidinoalkyl carboxy, where $Q_5$ is a side chain of an amino acid, and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, substituted or unsubstituted alkyl, substituted or unsubstituted hydroxyalkyl, substituted or unsubstituted alkyloxyalkyl, substituted or unsubstituted aminoalkyl, substituted or unsubstituted aryl, substituted or unsubstituted haloalkyl, substituted or unsubstituted alkenyl, substituted or unsubstituted alkynyl, oxo, linking group attached to a second CSA, substituted or unsubstituted aminoalkyloxy, substituted or unsubstituted aminoalkylcarboxy, substituted or unsubstituted aminoalkylaminocarbonyl, substituted or unsubstituted di(alkyl)aminoalkyl, $H_2N$—$HC(Q_5)$-$C(O)$—$O$—, $H_2N$—$HC(Q_5)$-$C(O)$—$N(H)$—, azidoalkyloxy, cyanoalkyloxy, P.G.-HN—$HC(Q_5)$-$C(O)$—$O$—, guanidinoalkyloxy, and guanidinoalkylcarboxy, where Qs is a side chain of an amino acid, and P.G. is an amino protecting group, provided that at least two of $R_{1-4}$, $R_6$, $R_7$, $R_{11}$, $R_{12}$, $R_{15}$, $R_{16}$, $R_{17}$, and $R_{18}$ are independently selected from the group consisting of substituted or unsubstituted aminoalkyl, substituted or unsubstituted aminoalkyloxy, substituted or unsubstituted alkylcarboxyalkyl, substituted or unsubstituted alkylaminoalkylamino, substituted or unsubstituted alkylaminoalkylaminoalkylamino, substituted or unsubstituted aminoalkylcarboxy, substituted or unsubstituted arylaminoalkyl, substituted or unsubstituted aminoalkyloxyaminoalkyl-aminocarbonyl, substituted or unsubstituted aminoalkylaminocarbonyl, substituted or unsubstituted aminoalkylcarboxyamido, quaternary ammonium alkylcarboxy, substituted or unsubstituted di(alkyl)aminoalkyl, $H_2N$—$HC(Q_5)$-$C(O)$—$O$—, $H_2N$—$HC(Q_5)$-$C(O)$—$N(H)$—, azidoalkyloxy, cyanoalkyloxy, P.G.-HN—$HC(Q_5)$-$C(O)$—$O$—, substituted or unsubstituted guanidinoalkyloxy, and substituted or unsubstituted guanidinoalkylcarboxy.

2. The method of claim 1, wherein $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, substituted or unsubstituted ($C_1$-$C_{18}$) alkyl, substituted or unsubstituted ($C_1$-$C_{18}$) hydroxyalkyl, substituted or unsubstituted ($C_1$-$C_{18}$) alkyloxy-($C_1$-$C_{18}$) alkyl, substituted or unsubstituted ($C_1$-$C_{18}$) alkylcarboxy-($C_1$-$C_{18}$) alkyl, substituted or unsubstituted ($C_1$-$C_{18}$) alkylamino-($C_1$-$C_{18}$)alkyl, substituted or unsubstituted ($C_1$-$C_{18}$) alkylamino-($C_1$-$C_{18}$) alkylamino, substituted or unsubstituted ($C_1$-$C_{18}$) alkylamino-($C_1$-$C_{18}$) alkylamino-($C_1$-$C_{18}$) alkylamino, substituted or unsubstituted ($C_1$-$C_{18}$) aminoalkyl, substituted or unsubstituted aryl, substituted or unsubstituted arylamino-($C_1$-$C_{18}$) alkyl, substituted or unsubstituted ($C_1$-$C_{18}$) haloalkyl, substituted or unsubstituted $C_2$-$C_6$ alkenyl, substituted or unsubstituted $C_2$-$C_6$ alkynyl, oxo, linking group attached to a second CSA, substituted or unsubstituted ($C_1$-$C_{18}$) aminoalkyloxy, substituted or unsubstituted ($C_1$-$C_{18}$) aminoalkyloxy-($C_1$-$C_{18}$) alkyl, substituted or unsubstituted ($C_1$-$C_{18}$) aminoalkylcarboxy, substituted or unsubstituted ($C_1$-$C_{18}$) aminoalkylaminocarbonyl, substituted or unsubstituted ($C_1$-$C_{18}$) aminoalkyl-carboxamido, substituted or unsubstituted di($C_1$-$C_{18}$ alkyl)aminoalkyl, $H_2N$—$HC(Q_5)$-$C(O)$—$O$—, $H_2N$—$HC(Q_5)$-$C(O)$—$N(H)$—, substituted or unsubstituted ($C_1$-$C_{18}$) azidoalkyloxy, substituted or unsubstituted ($C_1$-$C_{18}$) cyanoalkyloxy, P.G.-HN—$HC(Q_5)$-$C(O)$—$O$—, substituted or unsubstituted ($C_1$-$C_{18}$) guanidinoalkyloxy, substituted or unsubstituted ($C_1$-$C_{18}$) quaternary ammonium alkylcarboxy, and substituted or unsubstituted ($C_1$-$C_{18}$) guanidinoalkyl carboxy, where Qs is a side chain of an amino acid, and P.G. is an amino protecting group;

$R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, substituted or unsubstituted ($C_1$-$C_{18}$) alkyl, substituted or unsubstituted ($C_1$-$C_{18}$) hydroxyalkyl, substituted or unsubstituted ($C_1$-$C_{18}$) alkyloxy-($C_1$-$C_{18}$) alkyl, substituted or unsubstituted ($C_1$-$C_{18}$) aminoalkyl, substituted or unsubstituted aryl, substituted or unsubstituted ($C_1$-$C_{18}$) haloalkyl, substituted or unsubstituted ($C_2$-$C_6$) alkenyl, substituted or unsubstituted ($C_2$-$C_6$) alkynyl, oxo, a linking group attached to a second CSA, substituted or unsubstituted ($C_1$-$C_{18}$) aminoalkyloxy, substituted or unsubstituted ($C_1$-$C_{18}$) aminoalkylcarboxy, substituted or unsubstituted ($C_1$-$C_{18}$) aminoalkylaminocarbonyl, substituted or unsubstituted di($C_1$-$C_{18}$alkyl)aminoalkyl, $H_2N$—$HC(Q_5)$-$C(O)$—$O$—, $H_2N$—$HC(Q_5)$-$C(O)$—$N(H)$—, substituted or unsubstituted ($C_1$-$C_{18}$) azidoalkyloxy, substituted or unsubstituted ($C_1$-$C_{18}$) cyanoalkyloxy, P.G.-HN—$HC(Q_5)$-$C(O)$—$O$—, substituted or unsubstituted ($C_1$-$C_{18}$) guanidinoalkyloxy, and ($C_1$-$C_{18}$) guanidinoalkylcarboxy, where $Q_5$ is a side chain of an amino acid, and P.G. is an amino protecting group;

provided that at least two of $R_{1-4}$, $R_6$, $R_7$, $R_{11}$, $R_{12}$, $R_{15}$, $R_{16}$, $R_{17}$, and $R_{18}$ are independently selected from the group consisting of substituted or unsubstituted ($C_1$-$C_{18}$) aminoalkyl, substituted or unsubstituted ($C_1$-$C_{18}$) aminoalkyloxy, substituted or unsubstituted ($C_1$-$C_{18}$) alkylcarboxy-($C_1$-$C_{18}$) alkyl, substituted or unsubstituted ($C_1$-$C_{18}$) alkylamino-($C_1$-$C_{18}$) alkylamino, substituted or unsubstituted ($C_1$-$C_{18}$) alkylamino-($C_1$-$C_{18}$) alkylamino ($C_1$-$C_{18}$) alkylamino, substituted or unsubstituted ($C_1$-$C_{18}$) aminoalkylcarboxy, substituted or unsubstituted arylamino ($C_1$-$C_{18}$) alkyl, substituted or unsubstituted ($C_1$-$C_{18}$) aminoalkyloxy ($C_1$-$C_{18}$) aminoalkylaminocarbonyl, substituted or unsubstituted ($C_1$-$C_{18}$) aminoalkylaminocarbonyl, substituted or unsubstituted ($C_1$-$C_{18}$) aminoalkylcarboxyamido, a substituted or unsubstituted ($C_1$-$C_{18}$) quaternary ammonium alkylcarboxy, substituted or unsubstituted di($C_1$-$C_{18}$alkyl)aminoalkyl, $H_2N$—$HC(Q_5)$-$C(O)$—$O$—, $H_2N$—$HC(Q_5)$-$C(O)$—$N(H)$-, substituted or unsubstituted ($C_1$-$C_{18}$) azidoalkyloxy, substituted or unsubstituted ($C_1$-$C_{18}$) cyanoalkyloxy, P.G.-HN—$HC(Q_5)$-$C(O)$—$O$—, substituted or unsubstituted ($C_1$-$C_{18}$) guanidinoalkyloxy, and substituted or unsubstituted ($C_1$-$C_{18}$) guanidinoalkylcarboxy.

3. The method of claim 2, wherein $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkyl-carboxamido, an unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy;

$R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, ($C_1$-$C_{18}$) alkylamino-($C_1$-$C_{18}$) alkylamino, unsubstituted ($C_1$-$C_{18}$) alkylamino-($C_1$-$C_{18}$) alkylamino- ($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy;

provided that at least two of $R_{1-4}$, $R_6$, $R_7$, $R_{11}$, $R_{12}$, $R_{15}$, $R_{16}$, $R_{17}$, and $R_{18}$ are independently selected from the group consisting of of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted alkylamino-($C_1$-$C_{18}$)alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino- ($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy.

4. The method of claim 3, wherein the non-isotopically labeled and radio-stable CSA, or a pharmaceutically acceptable salt thereof, is selected from the compound of Formula (II):

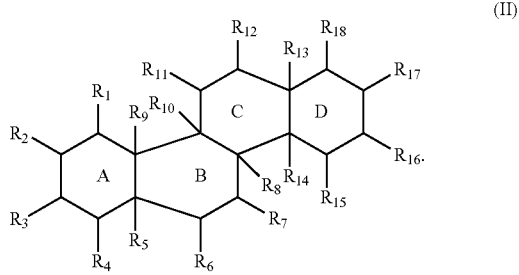

(II)

5. The method of claim 4, wherein rings A, B, C, and D are independently saturated.

6. The method of claim 5, wherein $R_3$, $R_7$, $R_{12}$, and $R_{18}$ are independently selected from the group consisting of hydrogen, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino- ($C_1$-$C_{18}$) alkylamino, an unsubstituted ($C_1$-$C_{18}$) aminoalkyl, an unsubstituted arylamino-($C_1$-$C_{18}$) alkyl, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy; and $R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and unsubstituted ($C_1$-$C_6$) alkyl.

7. The method of claim 6, wherein $R_3$, $R_7$, $R_{12}$, and $R_{18}$ are independently selected from the group consisting of hydrogen, an unsubstituted ($C_1$-$C_6$) alkyl, unsubstituted ($C_1$-$C_6$) hydroxyalkyl, unsubstituted ($C_1$-$C_{16}$) alkyloxy-($C_{1-5}$) alkyl, unsubstituted ($C_1$-$C_{16}$) alkylcarboxy-($C_1$-$C_5$) alkyl, unsubstituted ($C_1$-$C_{16}$) alkylamino-($C_{1-5}$)alkyl, ($C_1$-$C_{16}$) alkylamino-($C_1$-$C_5$) alkylamino, unsubstituted ($C_1$-$C_{16}$) alkylamino-($C_1$-$C_{16}$) alkylamino-($C_1$-$C_5$) alkylamino, an unsubstituted ($C_1$-$C_{16}$) aminoalkyl, an unsubstituted arylamino-($C_1$-$C_5$) alkyl, an unsubstituted ($C_1$-$C_5$) aminoalkyloxy, an unsubstituted ($C_1$-$C_{16}$) aminoalkyloxy-($C_1$-$C_5$) alkyl, an unsubstituted ($C_1$-$C_5$) aminoalkylcarboxy, an unsubstituted ($C_1$-$C_5$) aminoalkylaminocarbonyl, an unsubstituted ($C_1$-$C_5$) aminoalkylcarboxamido, an unsubstituted di($C_1$-$C_5$ alkyl)amino-($C_1$-$C_5$) alkyl, unsubstituted ($C_{1-5}$) guanidinoalkyloxy, unsubstituted ($C_1$-$C_{16}$) quaternary ammonium alkylcarboxy, and unsubstituted ($C_1$-$C_{16}$) guanidinoalkylcarboxy.

8. The method of claim 7, wherein $R_1$, $R_2$, $R_4$, $R_5$, $R_6$, $R_8$, $R_{10}$, $R_{11}$, $R_{14}$, $R_{16}$, and $R_{17}$ are each hydrogen; and $R_9$ and $R_{13}$ are each methyl.

9. The method of claim 8, wherein $R_3$, $R_7$, and $R_{12}$ are independently selected from the group consisting of aminoalkyloxy and aminoalkylcarboxy; and $R_{18}$ is selected from the group consisting of alkylaminoalkyl; alkoxycarbonylalkyl; alkylcarbonyloxyalkyl; di(alkyl)aminoalkyl; alkylaminoalkyl; alkyoxycarbonylalkyl; and alkylcarboxyalkyl.

10. The method of claim 1, wherein $R_3$, $R_7$, $R_{12}$, and $R_{18}$ are independently selected from the group consisting of amino-$C_3$-alkyloxy; amino-$C_3$-alkyl-carboxy; $C_8$-alkylamino-$C_5$-alkyl; $C_8$-alkoxy-carbonyl-$C_4$-alkyl; $C_{10}$-alkoxycarbonyl-$C_4$-alkyl; $C_8$-alkyl-carbonyl-$C_4$-alkyl; di-($C_5$-alkyl)amino-$C_5$-alkyl; $C_{13}$-alkylamino-$C_5$-alkyl; $C_6$-alkoxycarbonyl-$C_4$-alkyl; $C_6$-alkyl-carboxy-$C_4$-alkyl; and $C_{16}$-alkylamino-$_5$-alkyl.

11. The method of claim 1, wherein the cancer is treated by the CSA contacting and killing cancer cells.

12. The method of claim 1, wherein the cancer of the gastrointestinal tract is selected from rectal cancer, colon cancer, and pancreatic cancer.

13. The method of claim 1, wherein the bone cancer is selected from multiple myeloma, sarcoma, and leukemia.

14. A method of therapeutically treating cancer, comprising:

identifying a patient in need of therapeutic treatment of a cancer selected from gastrointestinal tract cancer and bone cancer; and administering to the patient a therapeutically effective amount of a non-isotopically labeled and radio-stable cationic steroid antimicrobial (CSA) of Formula I, or a pharmaceutically acceptable salt thereof, in an amount so as to therapeutically treat the cancer by killing or reducing proliferation of cancerous cells:

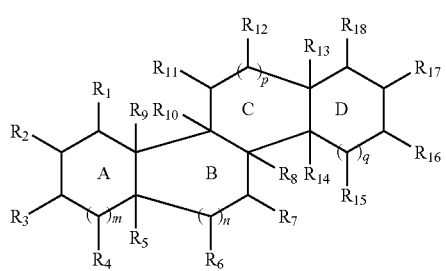

where,
rings A, B, C, and D are independently saturated, or are fully or partially unsaturated, provided that at least two of rings A, B, C, and D are saturated;

m, n, p, and q are independently 0 or 1;

$R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, substituted or unsubstituted alkyl, substituted or unsubstituted hydroxyalkyl, substituted or unsubstituted alkyloxyalkyl, substituted or unsubstituted alkylcarboxyalkyl, substituted or unsubstituted alkylaminoalkyl, substituted or unsubstituted alkylaminoalkylamino, substituted or unsubstituted alkylaminoalkylamino -alkylamino, substituted or unsubstituted aminoalkyl, substituted or unsubstituted aryl, substituted or unsubstituted arylaminoalkyl, substituted or unsubstituted haloalkyl, substituted or unsubstituted alkenyl, substituted or unsubstituted alkynyl, oxo, linking group attached to a second CSA, substituted or unsubstituted aminoalkyloxy, substituted or unsubstituted aminoalkyloxyalkyl, substituted or unsubstituted aminoalkylcarboxy, substituted or unsubstituted aminoalkylaminocarbonyl, substituted or unsubstituted aminoalkyl-carboxamido, substituted or unsubstituted di(alkyl)aminoalkyl, $H_2N—HC(Q_5)-C(O)—O—$, $H_2N—HC(Q_5)-C(O)—N(H)—$, substituted or unsubstituted azidoalkyloxy, substituted or unsubstituted cyanoalkyloxy, P.G.-HN—HC($Q_5$)-C(O)—O—, substituted or unsubstituted guanidinoalkyloxy, substituted or unsubstituted quaternary ammonium alkylcarboxy, and substituted or unsubstituted guanidinoalkyl carboxy, where $Q_5$ is a side chain of an amino acid, and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, substituted or unsubstituted alkyl, substituted or unsubstituted hydroxyalkyl, substituted or unsubstituted alkyloxyalkyl, substituted or unsubstituted aminoalkyl, substituted or unsubstituted aryl, substituted or unsubstituted haloalkyl, substituted or unsubstituted alkenyl, substituted or unsubstituted alkynyl, oxo, linking group attached to a second CSA, substituted or unsubstituted aminoalkyloxy, substituted or unsubstituted aminoalkylcarboxy, substituted or unsubstituted aminoalkylaminocarbonyl, substituted or unsubstituted aminoalkyl, $H_2N—HC(Q_5)-C(O)—O—$, $H_2N—HC(Q_5)-C(O)—N(H)—$, azidoalkyloxy, cyanoalkyloxy, P.G.-HN—HC($Q_5$)-C(O)—O—, guanidinoalkyloxy, and guanidinoalkylcarboxy, where $Q_5$ is a side chain of an amino acid, and P.G. is an amino protecting group, provided that at least two of $R_{1-4}$, $R_6$, $R_7$, $R_{11}$, $R_{12}$, $R_{15}$, $R_{16}$, $R_{17}$, and $R_{18}$ are independently selected from the group consisting of substituted or unsubstituted aminoalkyl, substituted or unsubstituted aminoalkyloxy, substituted or unsubstituted alkylcarboxyalkyl, substituted or unsubstituted alkylaminoalkylamino, substituted or unsubstituted alkylaminoalkylaminoalkylamino, substituted or unsubstituted aminoalkylcarboxy, substituted or unsubstituted arylaminoalkyl, substituted or unsubstituted aminoalkyloxyaminoalkyl-aminocarbonyl, substituted or unsubstituted aminoalkylaminocarbonyl, substituted or unsubstituted aminoalkylcarboxyamido, quaternary ammonium alkylcarboxy, substituted or unsubstituted di(alkyl)aminoalkyl, $H_2N—HC(Q_5)-C(O)—O—$, $H_2N—HC(Q_5)-C(O)—N(H)—$, azidoalkyloxy, cyanoalkyloxy, P.G.-HN—HC($Q_5$)-C(O)—O—, substituted or unsubstituted guanidinoalkyloxy, and substituted or unsubstituted guanidinoalkylcarboxy.

15. A method of therapeutically or prophylactically treating cancer, comprising:

identifying a patient in need of therapeutic or prophylactic treatment of cancer; and locally administering to tissue of the patient containing cancer cells a therapeutically effective amount of a non-isotopically labeled and radio-stable cationic steroid antimicrobial (CSA) of Formula I, or a pharmaceutically acceptable salt thereof, so as to therapeutically or prophylactically treat the cancer by killing or reducing proliferation of cancer cells:

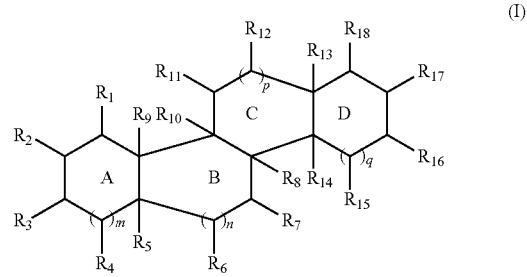

where,
rings A, B, C, and D are independently saturated, or are fully or partially unsaturated, provided that at least two of rings A, B, C, and D are saturated;

m, n, p, and q are independently 0 or 1;

$R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, substituted or unsubstituted alkyl, substituted or unsubstituted hydroxyalkyl, substituted or unsubstituted alkyloxyalkyl, substituted or unsubstituted alkylcarboxyalkyl, substituted or unsubstituted alkylaminoalkyl, substituted or unsubstituted alkylaminoalkylamino, substituted or unsubstituted alkylaminoalkylamino-alkylamino, substituted or unsubstituted aminoalkyl, substituted or unsubstituted aryl, substituted or unsubstituted arylaminoalkyl, substituted or unsubstituted haloalkyl, substituted or unsubstituted alkenyl, substituted or unsubstituted alkynyl, oxo, linking group attached to a second CSA, substituted or unsubstituted aminoalkyloxy, substituted or unsubstituted aminoalkyloxyalkyl, substituted or unsubstituted aminoalkylcarboxy, substituted or unsubstituted aminoalkylaminocarbonyl, substituted or unsubstituted aminoalkyl-carboxamido, substituted or unsubstituted di(alkyl)aminoalkyl, $H_2N-HC(Q_5)-C(O)-O-$, $H_2N-HC(Q_5)-C(O)-N(H)-$, substituted or unsubstituted azidoalkyloxy, substituted or unsubstituted cyanoalkyloxy, P.G.-HN—HC($Q_5$)-(O)—O—, substituted or unsubstituted guanidinoalkyloxy, substituted or unsubstituted quaternary ammonium alkylcarboxy, and substituted or unsubstituted guanidinoalkyl carboxy, where $Q_5$ is a side chain of an amino acid, and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, substituted or unsubstituted alkyl, substituted or unsubstituted hydroxyalkyl, substituted or unsubstituted alkyloxyalkyl, substituted or unsubstituted aminoalkyl, substituted or unsubstituted aryl, substituted or unsubstituted haloalkyl, substituted or unsubstituted alkenyl, substituted or unsubstituted alkynyl, oxo, linking group attached to a second CSA, substituted or unsubstituted aminoalkyloxy, substituted or unsubstituted aminoalkylcarboxy, substituted or unsubstituted aminoalkylaminocarbonyl, substituted or unsubstituted di(alkyl)aminoalkyl, $H_2N-HC(Q_5)-C(O)-O-$, $H_2N-HC(Q_5)-C(O)-N(H)-$, azidoalkyloxy, cyanoalkyloxy, P.G.-HN—HC($Q_5$)-C(O)—O—, guanidinoalkyloxy, and guanidinoalkylcarboxy, where $Q_5$ is a side chain of an amino acid, and P.G. is an amino protecting group, provided that at least two of $R_{1-4}$, $R_6$, $R_7$, $R_{11}$, $R_{12}$, $R_{15}$, $R_{16}$, $R_{17}$, and $R_{18}$ are independently selected from the group consisting of substituted or unsubstituted aminoalkyl, substituted or unsubstituted aminoalkyloxy, substituted or unsubstituted alkylcarboxyalkyl, substituted or unsubstituted alkylaminoalkylamino, substituted or unsubstituted alkylaminoalkylaminoalkylamino, substituted or unsubstituted aminoalkylcarboxy, substituted or unsubstituted arylaminoalkyl, substituted or unsubstituted aminoalkyloxyaminoalkylamino-carbonyl, substituted or unsubstituted aminoalkylaminocarbonyl, substituted or unsubstituted aminoalkylcarboxyamido, quaternary ammonium alkylcarboxy, substituted or unsubstituted di(alkyl)aminoalkyl, $H_2N-HC(Q_5)-C(O)-O-$, $H_2N-HC(Q_5)-C(O)-N(H)-$, azidoalkyloxy, cyanoalkyloxy, P.G.-HN—HC($Q_5$)-C(O)—O—, substituted or unsubstituted guanidinoalkyloxy, and substituted or unsubstituted guanidinoalkylcarboxy.

16. The method of claim 15, wherein the cancer is a carcinoma.

17. The method of claim 15, wherein the cancer is a sarcoma.

18. The method of claim 15, wherein the cancer is a lymphoma or multiple myeloma.

19. The method of claim 15, wherein the cancer is cancer of the gastrointestinal tract.

20. The method of claim 15, wherein the cancer is bone cancer.

* * * * *